(12) United States Patent
Boyer et al.

(10) Patent No.: US 10,034,775 B2
(45) Date of Patent: Jul. 31, 2018

(54) CONTACT SURFACE ADAPTER AND COMPONENTS FOR ARTIFICIAL PROSTHESIS INSTALLATION CLAMP

(71) Applicant: Boyer Anderson, LLC, Henrico, VA (US)

(72) Inventors: John Stuart Boyer, Henrico, VA (US); Bruce Reed Anderson, Richmond, VA (US)

(73) Assignee: Boyer Anderson, LLC, Henrico, VA (US)

( * ) Notice: Subject to any disclaimer, the term of this patent is extended or adjusted under 35 U.S.C. 154(b) by 0 days.

(21) Appl. No.: 15/469,165

(22) Filed: Mar. 24, 2017

(65) Prior Publication Data

US 2017/0196703 A1 Jul. 13, 2017

Related U.S. Application Data

(60) Division of application No. 15/117,288, filed as application No. PCT/US2015/043406 on Aug. 3, 2015, now Pat. No. 9,603,721, which is a continuation-in-part of application No. 14/575,160, filed on Dec. 18, 2014, now Pat. No. 9,131,974.

(60) Provisional application No. 62/170,315, filed on Jun. 3, 2015, provisional application No. 62/031,946, filed on Aug. 1, 2014.

(51) Int. Cl.
*A61F 2/46* (2006.01)
*B25B 5/10* (2006.01)

(52) U.S. Cl.
CPC .............. *A61F 2/461* (2013.01); *B25B 5/101* (2013.01); *B25B 5/102* (2013.01); *A61F 2002/4622* (2013.01)

(58) Field of Classification Search
CPC .......... A61B 17/122; A61B 2017/2808; A61B 17/7047; B25B 5/16; A61F 2/461
See application file for complete search history.

(56) References Cited

U.S. PATENT DOCUMENTS

| | | | |
|---|---|---|---|
| 315,464 A | 4/1885 | Blessing | |
| 1,403,580 A | 1/1922 | Venema | |
| 2,579,995 A | 12/1951 | Atchison | |
| 3,052,462 A | 9/1962 | Butler | |
| 3,151,897 A | 10/1964 | Wagner | |
| 5,021,055 A | 6/1991 | Burkinshaw et al. | |

OTHER PUBLICATIONS

International Search Report and Written Opinion (ISR/WO), PCT/US15/43406, US International Search Authority, Oct. 29, 2015.

*Primary Examiner* — Andrew Yang
(74) *Attorney, Agent, or Firm* — Williams Mullen; Thomas F. Bergert

(57) ABSTRACT

In the use of devices and methods for measuring applied pressure on an article, such as a patella construct during a surgical procedure, differently sized and configured clamp bushing adapters can be interchangeably employed with, and removably secured to, a clamp stem to adapt to the relative sizes of objects being clamped. Embodiments of an installation cap can also be provided to assist with proper setup and operation by, for example, removably covering spike elements associated with a working surface of embodiments of the device.

10 Claims, 16 Drawing Sheets

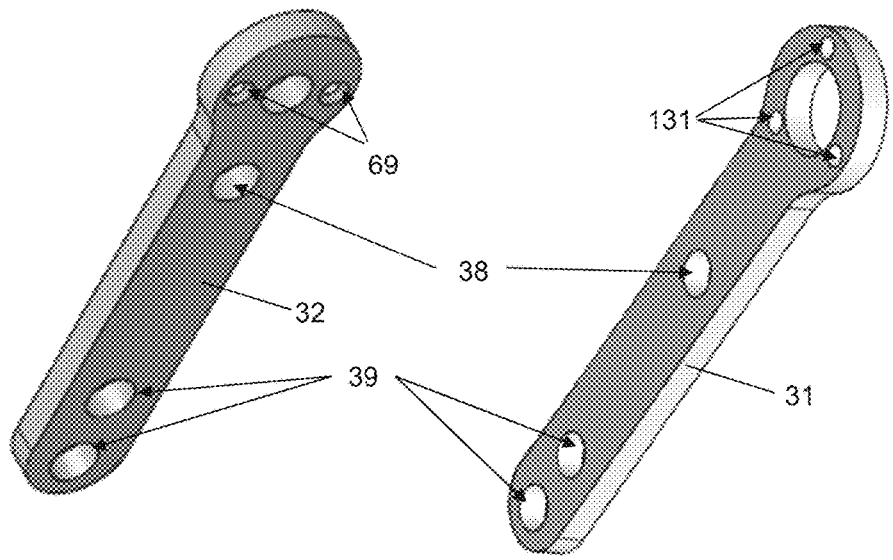

CONTACT SURFACE ADAPTER AND COMPONENTS FOR ARTIFICIAL PROSTHESIS INSTALLATION CLAMP

TECHNICAL FIELD

The present invention relates to medical instrumentation, and more particularly to a device for adapting the contact surface or surfaces of an artificial prosthesis installation clamp.

BACKGROUND ART

The typical known art of surgically resurfacing the natural patella, when necessary to accept an artificial patella prosthesis, requires the patella to be everted and held in a position allowing the surgeon to have access to the articulating surface which normally articulates within the intercondylar notch between the femoral condyles.

The natural patella is first measured, establishing its exact thickness, after which the surgeon resects the appropriate thickness of the posterior portion of the natural patella, and then prepares the surface to receive the artificial patella prosthesis. A patella trial replicating the actual implant to be installed is placed upon the prepared patella surface to confirm proper fit and thickness of the patella construct that establishes proper ligamentus tension for optimum stability and range of motion whereupon, a bonding agent (e.g., bone cement) is prepared. In the typical known handling of the bone cement, there is an exact science of measured polymer (e.g., powder) and monomer (e.g., liquid) packaged sterile in their individual respective states delivered into a sterile field placed into and enclosed in a sterile container whereupon measured vacuum force is applied and a measured time of thorough mixing is conducted. The properties are handled under strict scrutiny and respectful disciplines. When the vacuum is released, the top of the sterile container can be removed, giving access to the bone cement, whereupon it is examined to confirm that it is in the proper state to be applied. Precautions are generally taken to create the bone cement and bring it into a proper stable useable product, whereby it can be applied in order to successfully bond the aforementioned surfaces. At this juncture, a patella clamp is applied to the patella construct (which consists of the surgically resurfaced posterior aspect of natural patella prepared to receive an artificial patella replacement paired with the bonding agent bone cement). However, past methods and devices for applying the pressure have not been controlled and have resulted in the application of an arbitrary and unknown pressure upon the patella construct until the bone cement is fully cured. As such, less than satisfactory results can occur.

Measured pressure upon the patella construct is a paramount consideration to the mechanical properties, scientific quantitation and increased long-term success of the bonding integrity of the bone cement. Heretofore, no patella clamp has existed for general surgical use which takes into account all the parameters and dynamics taking place within the patella construct as it relates to all surfaces involved and the scientific and mechanical properties of the bonding agent bone cement during installation, as well as, the potential of excessive unknown pressure upon the host patella creating micro fractures. Further, past patella clamps have not addressed the need for contact surface adapters and components that protect the user during and after preparation and operation while providing a disposable component facilitating accurate relative sizing and post-operative cleaning.

DISCLOSURE OF INVENTION

In various aspects, the present invention enables the medical professional (e.g., a surgeon) to accurately apply positive linear directional control and known pressure upon the patella construct throughout the process to the cure state of the bone cement, while protecting the professional during and after preparation and operation while providing a disposable component facilitating accurate relative sizing and post-operative cleaning. After the initial proper pressure is established upon the patella construct, certain variables can come into play affecting the applied pressure. In various aspects, the present invention allows the attending medical professional(s) to stay informed as to pressure changes, giving the medical professional(s) the capability to re-establish correct pressure by known positive control.

Aspects and embodiments of the current inventive device receive the everted patella in its prepared form whereupon the anterior portion of the natural patella is placed upon a spiked platform of a bottom plate associated with the various embodiments of the device. The adapter and components according to embodiments of the present invention cover the spiked platform before and after use while further providing a disposable component facilitating accurate relative sizing and post-operative cleaning. Upon the patella being held in place, the surgeon or other medical professional takes hold of the knob of the knob assembly of the present device, holding it firmly in one hand. With the other hand, the medical professional depresses a quick release button of one embodiment of the present device, freeing the adjustment rod thereupon. As the medical professional pushes downward atop the knob in this embodiment, the indicating assembly of the present device translates downward in a controlled linear direction as its slide ring houses and translates upon the keyed guide rod acting as an established vertical stable construct. When the patella bushing or adapter device of the present invention makes contact with the artificial patella of the patella construct, the medical professional can apply controlled pressure, and an indicating assembly measures the pressure being applied and an assembly contained calibrated indicator gives visual knowledge and reference as to the precise amount of measured applied pressure being applied.

In alternative embodiments, a medical professional secures an appropriately sized and configured insert into the device, ensures that the everted patella is appropriately situated in the receiving area of the device, and adjusts a knob assembly to a desired level associated with a measured pressure.

Upon the surgeon creating the specific required and known applied pressure, the clockwise turning motion upon the assembly knob can be terminated. At this time, the bonding agent within the patella construct will squeegee out; the bottom platform spikes will depress into the anterior patella and the bushing (e.g., a rubber bushing or of other material and design) in the stem of the clamp indicating assembly can settle in. It will be appreciated that the above processes can take effect within seconds and the amount of applied pressure can thereafter decrease.

Thereupon, the present inventive device indicator visually informs the medical professional(s) of the potential adverse change in pressure and this calibrated reference gives the necessary information to correct and re-establish proper pressure. In the event of change from optimum applied pressure, the medical professional can create additional needed known applied pressure by again turning the assembly knob to re-establish the precise prescribed pressure to be upon the patella construct. The present invention thus, in part, enables the medical professional to create and maintain measured applied pressure upon the patella construct until the bone cement is fully cured. Upon the professional confirming the bone cement is fully cured, the present device can be removed by turning the knob in the opposite direction from the direction used to apply pressure, thereby relieving pressure off the indicating device. An adapter device secured to the clamp can then be discarded and the clamp device thoroughly cleaned, particularly around areas close to the operative procedure so as to be appropriately prepared for further use.

Among other things, the present invention substantially improves procedures in the installation of an artificial patella prosthetic replacement in total knee arthroplasty and is also introductory to additional improvements within a system of surgical instrumentation.

BRIEF DESCRIPTION OF THE DRAWINGS

FIG. 9 is a perspective view of an embodiment of a top plate employable with embodiments of the present invention.

FIG. 10 is a perspective view of an embodiment of a bottom base plate employable with embodiments of the present invention.

FIG. 11 is a perspective view of an embodiment of a portion of an actuator assembly employable with embodiments of the present invention.

MODES FOR CARRYING OUT THE INVENTION

Figure 1:
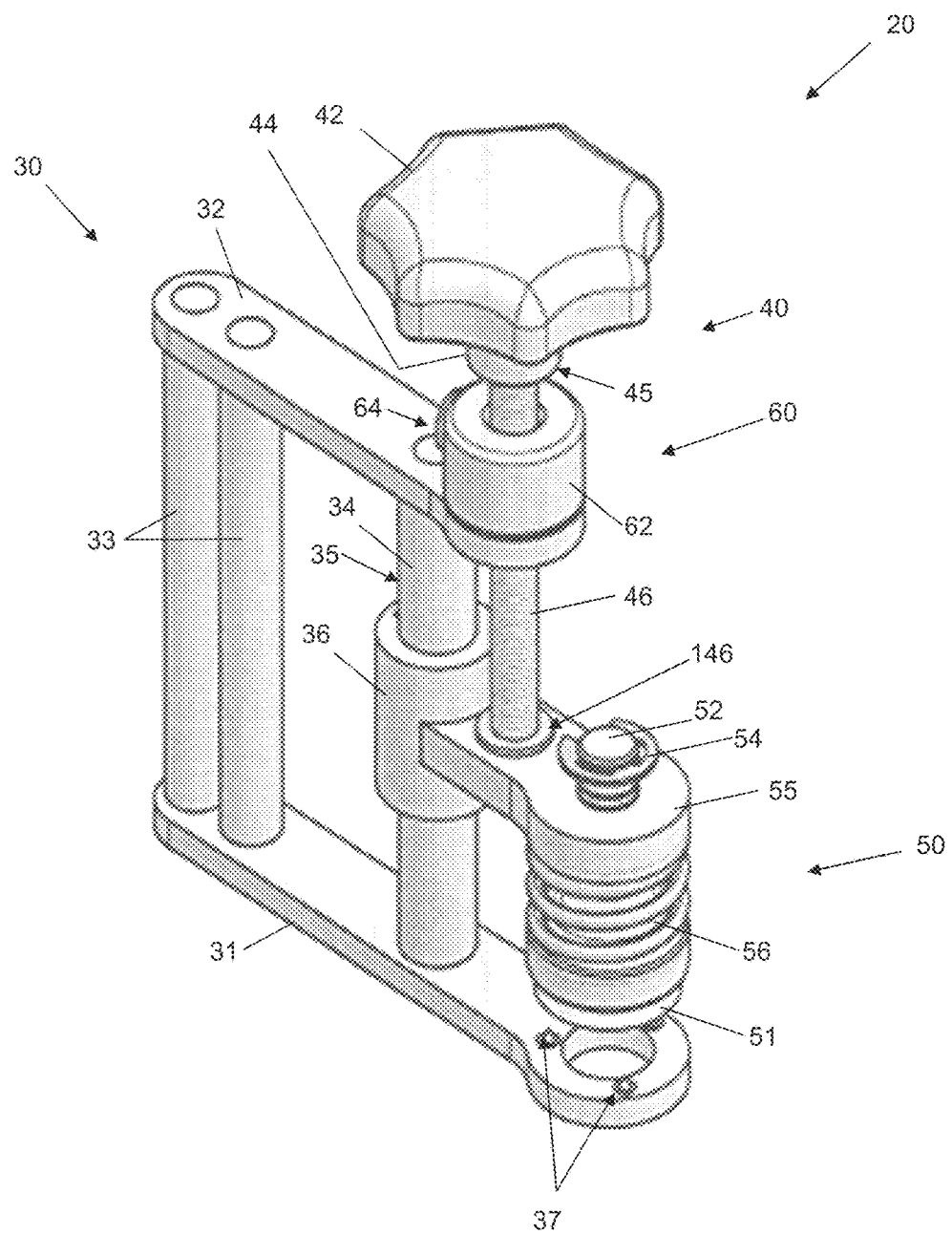
FIG. 1 is a perspective view of an assembled version of one embodiment of a clamp device employable with embodiments of the present invention.
Figure 2:
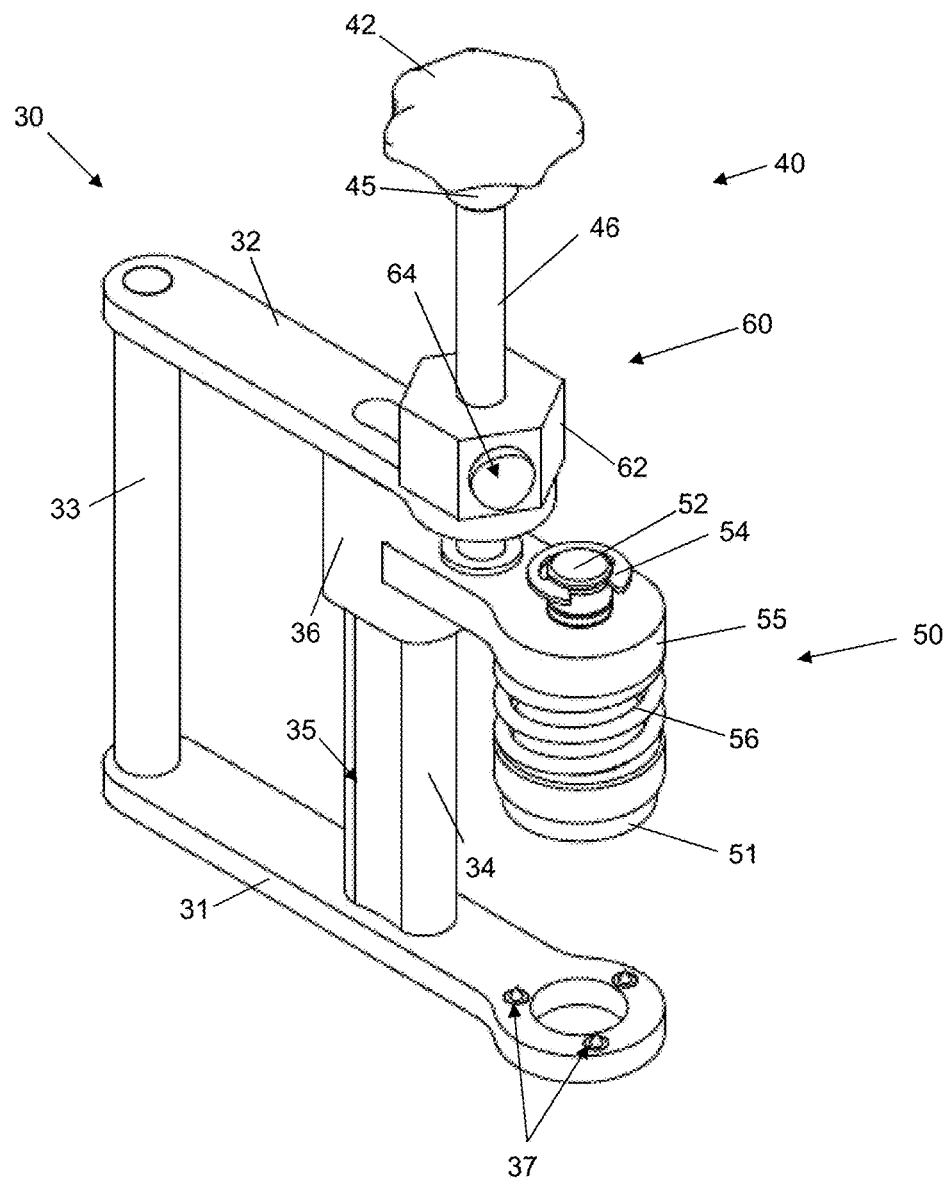
FIG. 2 is a perspective view of an assembled version of an alternative embodiment of a clamp device employable with embodiments of the present invention.

FIGS. 1 and 2 are perspective views of different embodiments of the adjustable measured applied pressure clamp device 20 for use with embodiments of the present invention. As shown in the embodiment in FIG. 1, the device 20 comprises a frame assembly 30 for receiving and maintaining a knob assembly 40 and a clamp indicating assembly 50.

The frame assembly 30 can comprise a bottom base plate 31 and a top plate 32, which are held apart in substantially parallel relation by a handle member 33 and a guide rod 34. In various embodiments, the base plate 31 includes one or more spikes 37 for use in assisting with holding an object being compressed during operation of the device associated with embodiments of the present invention. As shown in FIG. 10, openings 131 are provided in the base plate 31 to receive spikes. While the handle member 33 is shown in FIG. 1 as a pair of substantially cylindrical bodies secured to the bottom 31 and top 32 plates, it will be appreciated that the handle member 33 can take various forms without compromising the function of the present invention. For example, as shown in FIG. 2, the handle 33 can be a single member.

In the embodiment shown in FIG. 1, the guide rod 34 is a substantially cylindrical body secured to the bottom 31 and top 32 plates. In the embodiment shown in FIG. 2, the guide rod 34 is somewhat "peanut-shaped" in cross-section and is secured to the bottom 31 and top 32 plates. The guide rod 34 is positioned proximate to the knob assembly 40 and clamp indicating assembly 50, whereas the handle member 33 is positioned away from the knob assembly and clamp indicating assembly 50. The relative positioning of the handle member 33 and the guide rod 34 assists in ensuring that the plates 31 and 32 are maintained in stable position to facilitate operation of the device embodiments. In various embodiments, the frame assembly 30, including the plates 31, 32, the handle member 33 and the guide rod 34 can be formed of stainless steel, aluminum, plastic, brass and other materials of sufficient hardness and strength for the contemplated purposes and operations. Further, the handle member 33 and the guide rod 34 can be secured to the plates 31, 32 by being bolted, welded, soldered, pressed, captured and other known forms of connection. In embodiments (see FIGS. 9 and 10, for example), openings 39 in the plates 31, 32 facilitate the connection with the handle member(s) and openings 38 facilitate connection with the guide rod 34.

Figure 3:
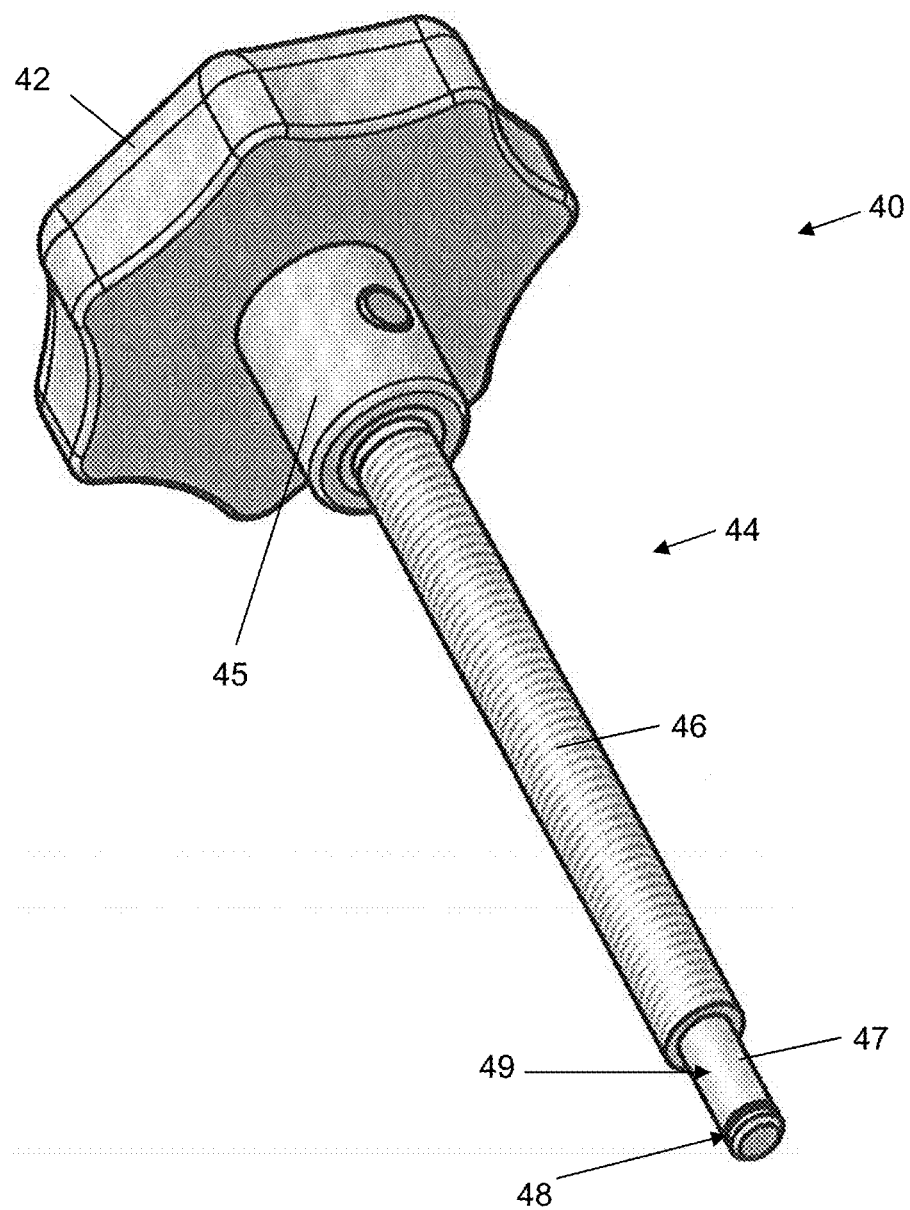
FIG. 3 is a perspective view of an embodiment of a knob assembly portion employable with embodiments of the present invention.

As shown in FIGS. 1 through 3, the knob assembly 40 employable with embodiments of the present invention can include a knob 42 and an adjustment rod 44. The knob 42 can be attached to the adjustment rod 44 by being pressed, bolted, welded, soldered, pinned, threaded or being integrally formed, for example. The adjustment rod 44 can include a base portion 45, an extension portion 46, and an extension segment 47 having a groove 48 formed in the outer surface 49 thereof. In embodiments, the base portion 45 is substantially cylindrical with a substantially smooth exterior and the extension portion 46 is also substantially cylindrical and includes a threaded exterior for engaging an actuator assembly 60 as described in more detail hereafter. The extension segment 47 extends axially outwardly of the extension portion 46 and is adapted to extend through top plate 32, the actuator sleeve 62 and into a slide platform 55 of the clamp indicating assembly 50, as described in more detail hereafter. A locking pin (not shown) can secure the knob assembly 40 to the slide platform 55 by firmly engaging the groove 48 after the extension segment 47 has passed through an opening 53 in slide platform 55 (see FIGS. 5 and 6). In this way, the knob assembly can influence the movement of the slide platform 55 and thus the clamp indicating assembly 50, as described in more detail hereafter.

As shown in FIGS. 1, 2 and 11, the actuator assembly 60 includes an actuator sleeve 62 and an actuator button 64 extending outwardly of the outer surface 63 of the actuator sleeve 62. The actuator sleeve 62 is formed with a substantially cylindrical opening 65 having a diameter D extending axially therethrough, wherein the opening 65 is adapted to receive the extension portion 46 of the adjustment rod 44 of the knob assembly 40. In various embodiments, the actuator button 64 is formed in communication with a substantially U-shaped backside ridge (not shown) on the inside of the sleeve 62, such that when the button 64 is at rest, the backside ridge extends radially inwardly of the opening 65, effectively reducing the diameter D of the opening 65. When the button 64 is depressed towards the outer surface 63 of the sleeve 62, the backside ridge on the inside of the sleeve 62 is move radially outwardly, thereby restoring the full diameter D to opening 65 and permitting free axial passage of the extension portion 46 inserted therethrough. When the button is released, the backside ridge engages the extension portion 46 and holds it in axial position until such time as the button is pressed again, or the knob is rotated. When the button 64 is in the relaxed position, the extension portion 46 of knob assembly 60 can still move axially through the opening 65; however, any such movement occurs through rotation of the extension portion 46 using knob 42, for example. In this way, the outer thread of the extension portion 46 threadedly engages the backside ridge of the actuator assembly 60 to thereby move through the actuator sleeve in a more controlled and slower manner than through straight axial movement when the button 64 is depressed. Thus, the height of the clamp indicating assembly 50 above the bottom plate 31 of the frame 30 can be quickly adjusted upwardly and downwardly by depressing the actuator button 64, yet can also be adjusted more slowly and in a finer and more calculated fashion when the button is in the relaxed position and not pressed. It will be appreciated that the actuator assembly 60 can be provided as any of a number of commercially available push-button actuators, and can be secured to an end of the top plate 31 by being bolted, welded, soldered, pressed, captured and through other known forms of connection. It will also be appreciated that the thickness and pitch of the thread can be altered through other designs to suit ergonomic demands. Other devices beyond that shown can be used to accomplish the same or similar functions as assembly 60. In embodiments of the present invention, openings 67 in the sleeve 62 and openings 69 in plate 31 (see FIGS. 9 and 11) facilitate this connection.

Figure 4:
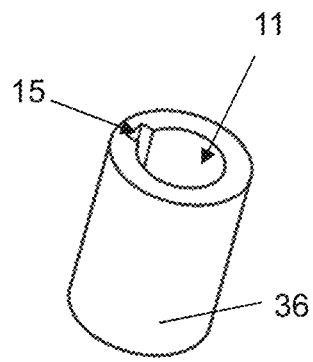
FIG. 4 is a perspective view of an embodiment of a guide rod sleeve employable with embodiments of the present invention.
Figure 5:
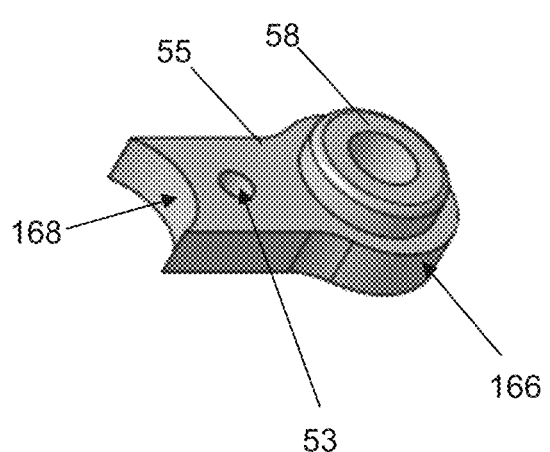
FIG. 5 is a perspective view of an embodiment of a slide platform portion of a clamp indicating assembly employable with embodiments of the present invention.
Figure 6:
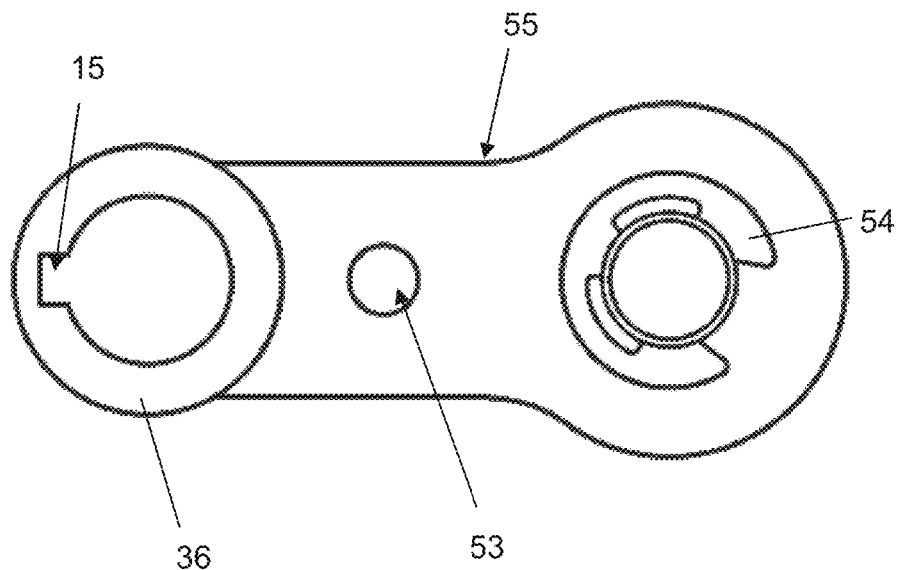
FIG. 6 is a top plan view of elements of an embodiment of a pressure monitor assembly employable with embodiments of the present invention.
Figure 7:
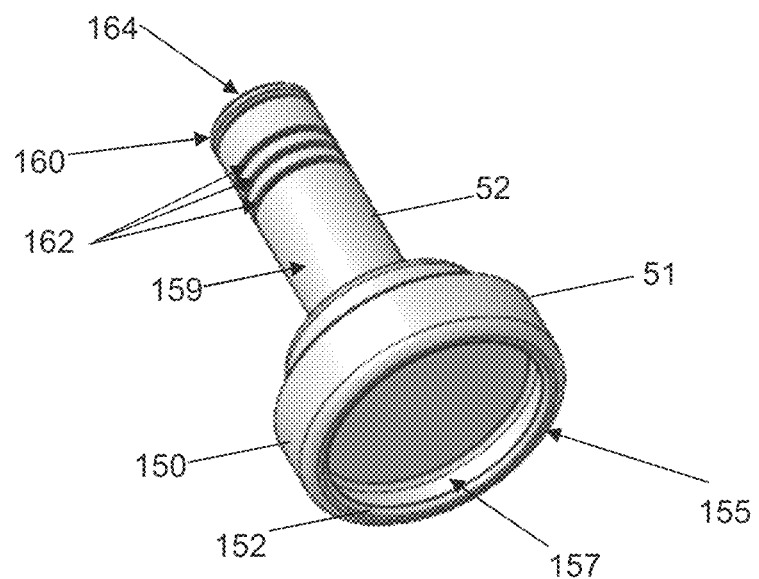
FIG. 7 is a perspective view of an embodiment of a stem assembly portion of a pressure monitor assembly employable with embodiments of the present invention.
Figure 8:
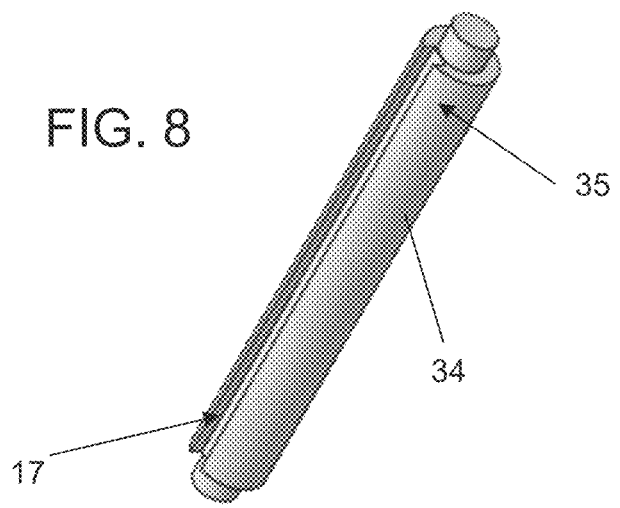
FIG. 8 is a perspective view of an embodiment of a guide rod employable with embodiments of the present invention.

As shown in FIGS. 1, 2 and 4 through 6, the clamp indicating assembly 50 is secured to the knob assembly 40 and the guide rod 34. In various embodiments, the guide rod 34 includes a flange member (not shown) extending radially outwardly along substantially the entire axially outer surface 35 of the rod 34. This flange member is adapted to engage the inner key opening 15 of the guide sleeve 36. In alternative embodiments, the guide rod 34 itself is keyed in the sense that it has a groove or depression 17 formed therein (see FIG. 8), wherein the groove 17 extends substantially axially along the outer surface 35 of the guide rod 34. This groove is adapted to receive an extension or flange member (not shown) of the guide rod sleeve 36. In either arrangement, the sleeve 36 can smoothly and movingly engage the guide rod 34 in linear fashion during operation of the present invention as will be described more completely hereafter. As shown in FIGS. 1, 4 and 6, the guide rod sleeve 36 is substantially cylindrical in shape, with an opening 11 extending axially therethrough, which permits the guide rod sleeve 36 to abut the outer surface 35 of the guide rod 34 for moving engagement therewith. It will be appreciated that other shapes of items 34 and 36 can be used to provide a guided single axis linear movement (see, for example, FIG. 2).

As shown in FIGS. 1, 2 and 5 through 7, the clamp indicating assembly 50 of the present invention can comprise a stem 52, a locking C-clip 54, a slide platform 55 and a load spring 56. These components assist in providing a mounting surface for mounting and articulating end effectors such as rubber or other material contactors that are used to press, hold or grip elements to be worked on during operation of the present invention, such as a patella or appliances used to replace portions of the patella, for example. Stem 52 can be used to assist in holding an element in position as additional devices aid in the patella restoration. Stem 52 also provides a bearing surface for linear movement during the function of applying pressure and provides a means of measurement. It can be used to rotate and orientate attachments. It can rotate to allow for easy use in various positions and accommodate left or right handed operators. The stem has a substantially hollow base portion 51 with a "major" or larger inner diameter defined by an outer wall 150 and a "minor" or smaller inner diameter defined by a lip 152 on the axially outer end 155 of the stem. The lip 152 helps to retain a bushing (not shown) inserted into the hollow opening 157 in the base portion 51. As further shown in FIG. 7, the stem includes a body portion outer surface 159 having substantially circumferential grooves 160, 162 formed therein. A first groove 160 is formed at an axially outer end portion 164 of the stem 52 and is cooperatively engageable with a clasping member, such as locking C-clip 54 shown in FIGS. 1 and 2. Other grooves 162 are measurement indicators that assist a user of the device in its various embodiments in understanding the amount of pressure being applied to a subject element, as will be described in more detail hereafter.

As further shown in FIGS. 1, 2, 5 and 6, the clamp indicating assembly 50 includes a slide platform 55 and load spring 56. The spring 56 can be positioned around stem 52, and the stem can then be inserted through opening 53 in the slide platform, after which the clip 54 can be locked into the groove 160 of stem 52. When locked, the stem 52 is then slidably maintained within the slide platform 55, and the clip 54 prevents the stem 52 from sliding all the way through the platform 55. However, the stem can be moved upward as shown in FIG. 1, where space exists between the clip 54 and the platform 55, and back down to a position where the clip 54 is in contact with and directly atop the platform 55, as shown in FIG. 2. In various embodiments, as shown in FIG. 5, for example, the slide platform 55 includes a spring guide extension 58 which extends from the inside surface 166 of the platform 55 and acts to retain the spring 56 in fixed radial position, such that the spring can only compress and extend, without moving from side to side. The platform 55 is also provided with a concave end surface 168 which is adapted to mate with the guide sleeve 36 in substantially flush relation. The platform 55 can be secured to the guide sleeve 36 in a variety of ways, including by being bolted, welded, soldered, pressed, captured and using other known forms of connection.

Embodiments of the device can be assembled after all manufacture related operations are complete by sliding spring 56 onto stem 52. These are now slid through opening 53 in platform 55 and clip 54 is snapped into the groove 160 on stem 52 creating assembly 50. Assembly 50 can now be slid onto guide rod 34 with the key and the slot aligned, as described above. This sub-assembly can now be set aside. Actuator assembly 60 can then be attached to top plate 32 using flat head screws or other connection, and this sub-portion can then be set aside. Handle member(s) 33 can then be positioned into alignment holes 39 on plate 31 and attached using button head screws or in another fashion. The previously assembled clamp indicating assembly 50 can then be secured to plates 31 and 32 with rod secured within openings 38 of plate 31 and 32. The assembly 50 can be visually aligned above the spikes 37. Now, actuator assembly 60 and knob assembly 40 are installed, and actuator assembly 60 is slid down until the tip of an adjusting screw is slightly above part 55. In various embodiments, an installer can visually make sure the tip of extension portion 46 of rod 44 aligns with the opening 53 in slide platform 55. A thrust washer 146 can then be installed onto the end of extension portion 46 (above the slide platform 55) and a locking clip installed underneath and into groove 48. The guide rod sleeve 36 should smoothly slide up and down on guide rod 34 when actuated by turning knob 42. When all alignment is established, any untightened connectors can be tightened as appropriate.

In exemplary embodiments, one can assume that a body part, such as the patella of a human knee, is being replaced or repaired. With the various embodiments described herein, measured pressure can be applied and accurate positioning accommodated in restoration of the patella, for example. In various aspects, other attachments to plate 31 or assemblies 50 and/or 60 can aid this and other surgeries where accurate pressure and positioning are needed. Other embodiments and components can be incorporated into or become new devices improving or replacing existing devices that now are outdated for their original purpose.

In a specific embodiment of operation, a medical professional such as a surgeon grasps the knob 42 of the knob assembly 40, then depresses the quick release button 64 on the actuator assembly 60. Upon depressing the quick release button 64, the adjustment rod 44 which passes through the actuator 62 and the top plate 32, and whose distal tip passes through the horizontal slide 55 is locked in place therein, is freed, allowing the slide 55 to translate vertically and parallel to the guide rod 34. This motion continues until the patella mating bushing attached to the base part 51 of the stem 52 makes direct contact with the artificial patella prosthesis. Upon full contact, the quick release button 64 is released, causing the thread engagement of the adjustment rod extension portion 46, whereupon the surgeon grasping the knob 42 can turn the knob in a clockwise motion, creating a controlled downward movement generating pressure upon the patella construct.

In fluid sequence, the stem portion 52 is then set and fixed upon the patella construct, passing through the load spring 56 which butts up on the horizontal slide 55 and the stem continues up through the horizontal slide 55 and is secured by a locking clip 54 at the most proximal part of the stem 52.

The artificial patella construct generally comprises an artificial patella prosthesis, followed by a bonding agent, followed by a natural patella that has been re-surfaced for facilitating best results in the knee replacement operation. The artificial patella prosthesis is positioned at the bottom of the clamp (in between the base plate 31 and the stem head 51. Then, the bonding agent, such as bone cement, is applied, and the natural resurfaced patella is then placed atop the bonding agent. Appropriate pressure must then be applied to properly secure the artificial patella prosthesis with the natural patella.

The first segment of the clamp indicating assembly to make contact with this patella construct is the bushing (not shown) which can be, for example, of a rubber material in a circular design to receive a button style artificial patella prosthesis. Other contact bushings of materials of plastic, metal and other designed to accept the geometric configuration of any artificial patella prosthesis replacement can be installed into the base 51 to facilitate operation of the present invention. The major inner diameter of the base 51 (described above) which receives the appropriate bushing and the minor diameter (described above) form an inner rim to serve as a locking mechanism to hold the specifically designed bushing securely in place. The stem grooves 162, which have been mathematically placed to serve as reference points for measuring pressure.

As the clamp indicating assembly 50 makes contact with the patella construct, the spikes 37 can engage the patella to hold it in place. As the surgeon continues to turn the knob 42 in clockwise motion, more pressure is evenly applied upon the construct, as the downward motion of the operative parts bear down, and the load spring 56 is compressed. As the load spring is compressed along with the respective assemblies moving downward, the stem proximal portion begins upward movement through the bore 53 of slide platform 55 as described above. The reference markings provided by grooves 162 indicate the exact measurement of pressure being applied. When the prescribed rate of pressure is achieved by the actions of the surgeon, the device can be held in position at the desired pressure for the desired length of time.

It will be appreciated that the present invention establishes the proper amount of measured applied pressure upon the patella construct on all involved and necessary surfaces. So after the initial establishment of pressure, all surfaces settle in the bone cement. To the extent the elements being compressed cause the pressure to change after initially being set, the pressure can be re-established. This is immediately revealed by visual assessment of the indicator grooves 162 of the device, which has not been available heretofore. Now a failure mode can be scientifically detected and mechanically corrected. The surgeon simply upon viewing the deficiency through the indicator grasps handle 33 in one hand and grasps knob 42 in the other, turning the knob in a clockwise motion with micro adjustment, thereby establishing or re-establishing the exact recommended pressure. The surgeon waits for full cure of the bones cement, and can verify this thereafter. To remove the device, the surgeon takes hold of handle 33 in one hand and grasps knob 42 with the other hand and turns the knob in counter clockwise motion to relieve the initial pressure of the device. Then with the hand that is on the handle 33, the surgeon can depress the quick release button 64 and pull straight up on knob 42, then release button 64 as the assembly locks in place. The device can then be removed.

It will be appreciated that aspects of the present invention can be provided such that the apparatus is "pre-set" to a desired or industry known or required pressure using a single action, such as by using actuator button 64.

FIGS. 12 through 21 show elements according to different embodiments of an adjustable measured applied pressure clamp device employable with embodiments the present invention. As shown in the embodiment in FIG. 12, the device 220 comprises a frame assembly 230 for receiving and maintaining a clamp assembly 270, which can include a knob assembly 300 and a pressure monitor assembly 330.

Figure 12:
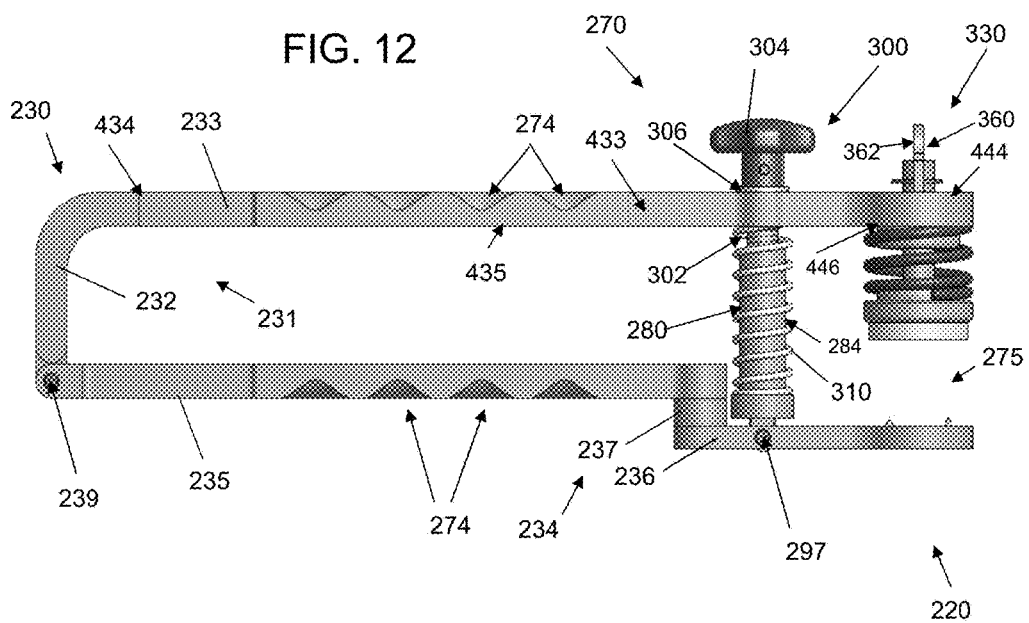
FIG. 12 is a front elevational view of an embodiment of an assembled version of a clamp device employable with embodiments of the present invention.
Figure 13:
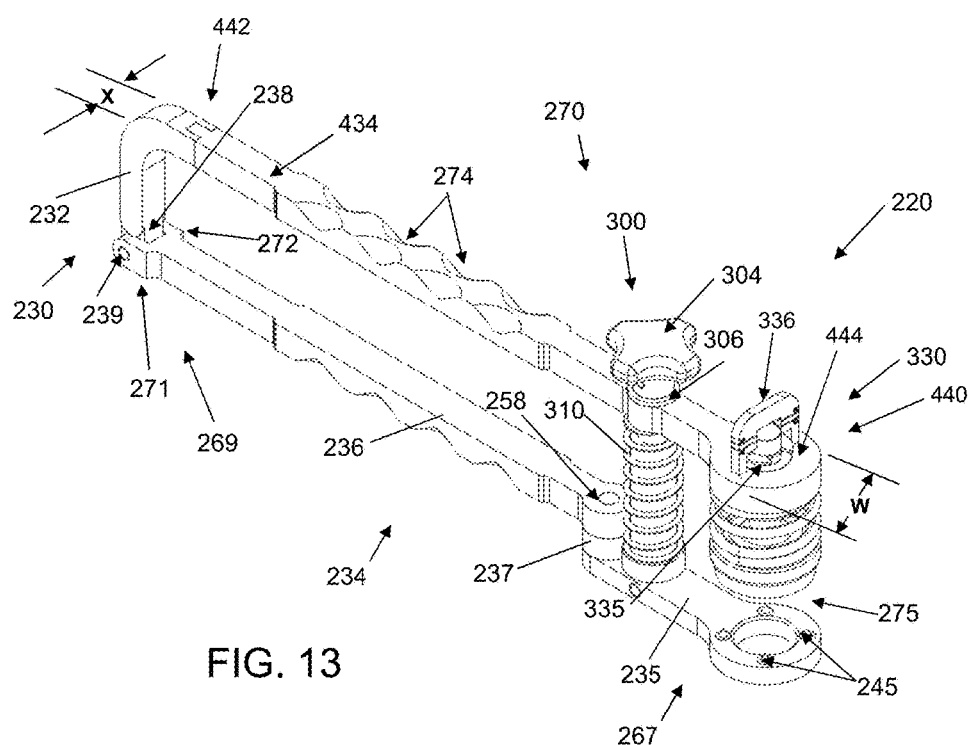
FIG. 13 is a perspective view of the embodiment of FIG. 12.

The frame assembly 230 can include an upper frame arm 231 and a lower frame arm 234. In various embodiments, the upper frame arm 231 and lower frame arm 234 comprise independent monolithic units. In other embodiments, the upper frame arm 231 and lower frame arm 234 can comprise multiple elements. The upper frame arm 231 can be referred to herein as an upper frame arm assembly and the lower frame arm 234 can be referred to herein as a lower frame arm assembly, regardless of whether each comprises a single monolithic unit or a multi-element arrangement. As shown, for example, in FIGS. 12 and 13, the lower frame arm assembly 234 comprises a fixed end element 235, a bottom handle element 236 and one or more spacer elements 237. As shown in FIG. 17, for example, the fixed end element 235 is provided with an extension portion 240, a clamp support portion 242, a top surface 244 and a bottom surface 246, with the top surface 244 of the clamp support portion 242 adapted to receive one or more spike elements 245 for receiving and securing elements of a patella construct or other item to be clamped or otherwise manipulated in the receiving area 275, in accordance with the present invention. For instance, the top surface 244 of the clamp support portion 242 can be provided with openings 248 that either extend through the fixed end element 235, or that are provided as blind holes that do not extend through the fixed end element 235, but which can securely receive the spike elements 245. The fixed end element 235 is also provided with a slot 250 extending through the top 244 and bottom 246 surfaces of the extension portion 235, and further a side opening 252 extending from a first side wall 254 to a second side wall (not shown) of the fixed end element 235, and passing through the slot 250. The slot 250 is adapted to receive a pivot nut 280 as shown in FIGS. 12 and 13, for example, and the pivot nut 280 is movably secured to the extension portion 240 of the fixed end element 235. With reference to FIGS. 12 through 17, in various embodiments, a pin 297 extends through the side walls (e.g., first side wall 254) and through an opening 296 in the pivot nut collar 294 when the pivot nut 280 is in position within the slot 250, in order to permit the pivot nut 280 to pivot during operation of the present invention.

As shown in FIG. 13, for example, the spacer element 237 can be provided with a substantially cylindrical body portion having an opening (not shown) therethrough for receiving a substantially cylindrical peg element 258. Alternatively, the peg element 258 and the spacer element 237 can be integrally formed as a monolithic unit. The peg element 258 is appropriately sized so as to be insertable within an opening 241 in the extension portion 240 of the fixed end element 235, and within an opening in the bottom handle element 236. In this way, the spacer element 237 helps secure the bottom handle element 236 to the fixed end element 235, and helps align the receiving area 275 of the device with the axis of the handle element 236. In this way, for example, the principles of operation of the device embodiments are enhanced. It will be appreciated that various embodiments can operate with multiple spacer elements such as element 237 in order to increase the area of the receiving area 275 for various sizes of articles and elements to be engaged in accordance with aspects of the present invention. In various embodiments where multiple spacer elements are employed, the spacer elements can be provided such that the peg element (e.g., 258) extends from an interior point within the opening of the cylindrical body portion to an external point outside of one side of the spacer element (e.g., 237). In this way, arrangements with multiple spacer elements can engage in a nested relationship, as a peg from a first spacer element is inserted into an opening of a second spacer element, and the peg from the second spacer element is inserted into the bottom handle element 236, the fixed end element 235, or another spacer element according to the employed arrangement.

As shown in FIGS. 12 and 13, the rear portion 269 of the lower frame arm assembly 234 is hingedly connected to the upper frame arm 231. The upper frame arm 231 can comprise a single monolithic arm, and can alternatively comprise a curved handle section 232 and a straight handle section 233, among other embodiments. The upper frame arm 231 can be hingedly secured to the lower frame arm assembly 234 in various ways. As shown in FIG. 13, for example, the curved handle section 232 of the upper frame arm 231 has a base portion 238 having an opening therethrough, which can receive a pin 239 that extends through edges 271, 272 of the rear portion 269 of the bottom handle element 236. As shown in FIGS. 12 and 13, the straight handle section 233 of the upper frame arm 231 and the bottom handle element 236 can further be provided with indentations or other forms of gripping elements 274 to facilitate operation. The straight handle section 233 includes side wall surfaces 433, a top surface 434 and a bottom surface 435, and in various embodiments, the indentations 274 are on one or more of the side wall surfaces 433.

Figure 15:
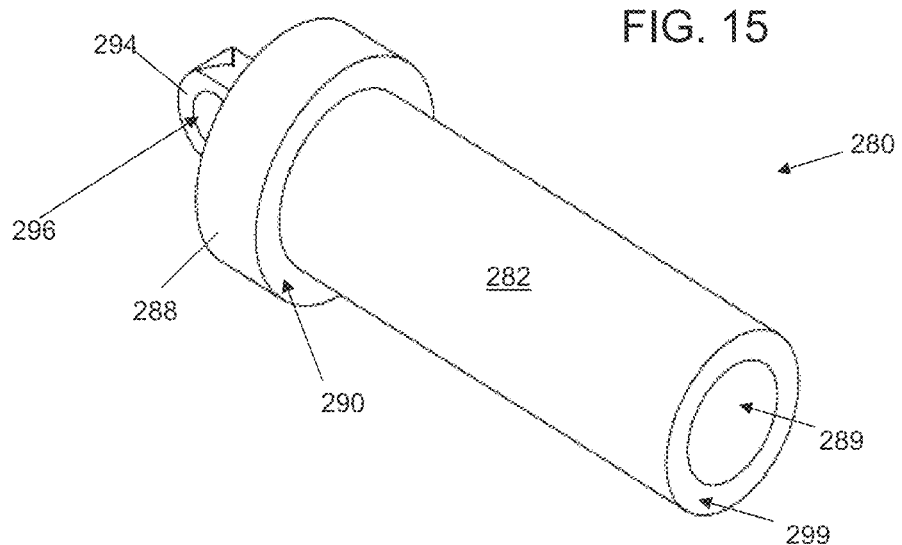
FIG. 15 is a perspective view of one embodiment of a pivot nut element employable with embodiments of the present invention.
Figure 16:
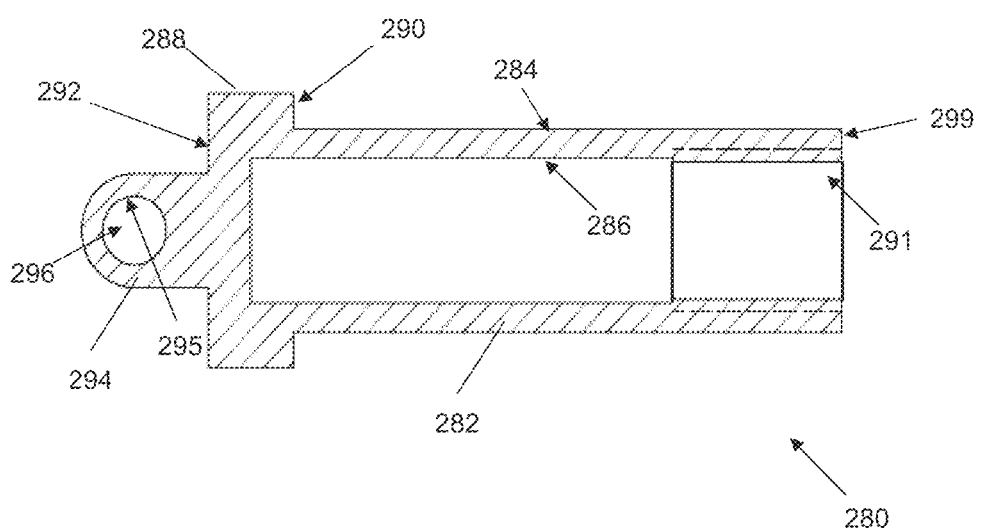
FIG. 16 is a front elevational view of the pivot nut element of FIG. 15.
Figure 17:
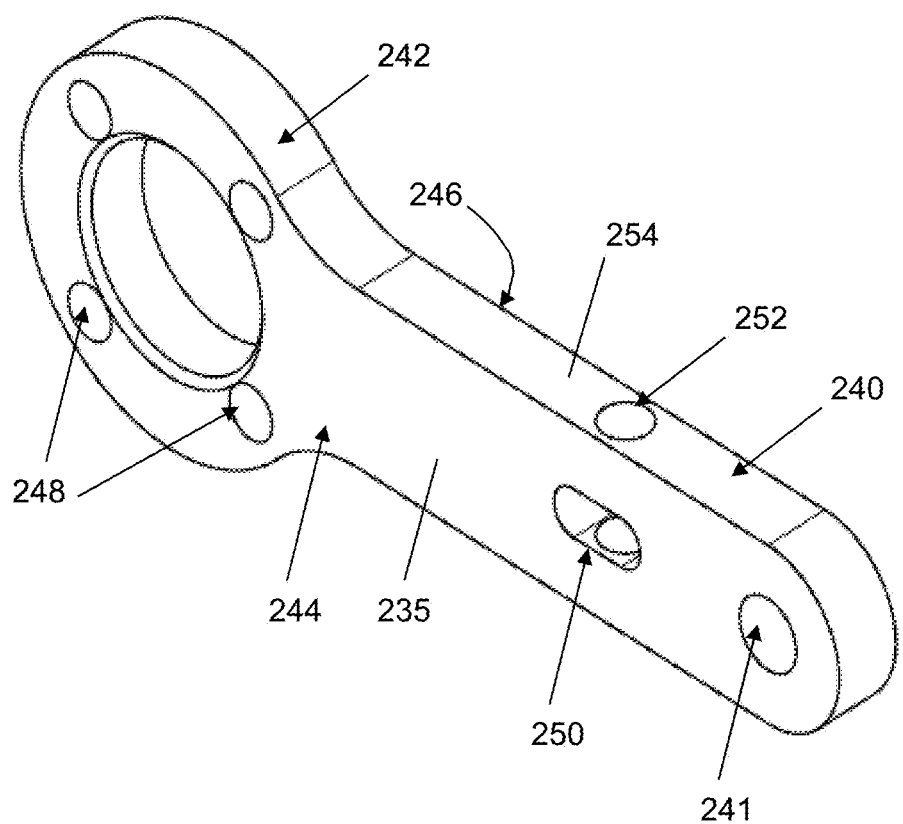
FIG. 17 is a perspective view of one embodiment of a bottom base plate employable with embodiments of the present invention.

As shown in the embodiments of FIGS. 12, 13, 15 and 16, the clamp assembly 270 includes a pivot nut 280, a knob assembly 300 and a spring member 310, with the pivot nut 280 pivotally secured to the fixed end element 235 at the front portion 267 of the lower frame arm assembly 234, as described above. In various embodiments, the spring member 310 and the pivot nut 280 can be considered part of the knob assembly 300 of the device of the present invention. As shown in FIGS. 15 and 16, the pivot nut 280 includes a substantially cylindrical body portion 282 having an exterior wall 284 and an interior wall 286, with the interior wall 286 forming an opening 289 in the body portion 282. In various embodiments, the axially outer portion 291 of the interior wall 286 is threaded so as to be capable of threadedly receiving an adjustment screw portion 302 of the knob assembly 300. In other embodiments, the full interior wall 286 is threaded. For example, the interior wall 286 can have a single female receiving thread extending the length of the wall, adapted to receive a male thread on the outer surface of the adjustment screw 302 (see FIG. 12). The threaded engagement of the adjustment screw portion 302 of the knob assembly 300 with the interior 286 of the pivot nut body portion 282 permits the embodiments of the device to operate so as to provide increasing or decreasing clamping pressure to the article in the receiving area 275, for example. As further shown in FIGS. 15 and 16, the pivot nut 280 includes a head portion 288 having a head surface 290 and a bottom surface 292, with a pivot collar 294 extending from the bottom surface 292. The pivot collar 294 can be substantially U-shaped in cross-section, with a gap 296 provided between the inner surface 295 of the pivot collar 294 and the bottom surface 292 of the pivot nut head 294. The gap 296 can receive the pin member 297 described above in order to permit the pivot nut 280 to pivot about the fixed end element 235. The pivot nut 280 is further provided with a receiving end 299, which can abut the bottom surface 435 of the upper arm 233 to provide a resistive surface to the knob assembly 300 when the knob 304 is being turned so as to tighten the clamping force on the object in the receiving area 275.

As shown in FIGS. 12 and 13, the adjustment screw 302 of the knob assembly 300 extends through an opening (not shown) in the upper frame arm 233 and engages the pivot nut 280. The knob assembly 300 further includes a knob 304 and a washer element 306. The knob 304 is securable to the adjustment screw 302, such that rotation of the knob 304 in one direction (e.g., clockwise) results in a tighter engagement of the screw 302 with the pivot nut 280, and rotation of the knob 304 in the opposite direction (e.g., counterclockwise) results in a loosening of the engagement between the screw 302 and pivot nut 280. Loosening thereby permits the upper arm 233 to raise higher, thereby permitting more space in the receiving area 275. As further shown in FIGS. 12 and 13, the spring member 310 can be positioned about the exterior wall 284 of the pivot nut body 282, engaging the head surface 290 of the pivot nut head portion 288, and also engaging the bottom surface 435 of the upper arm 233.

Figure 14:
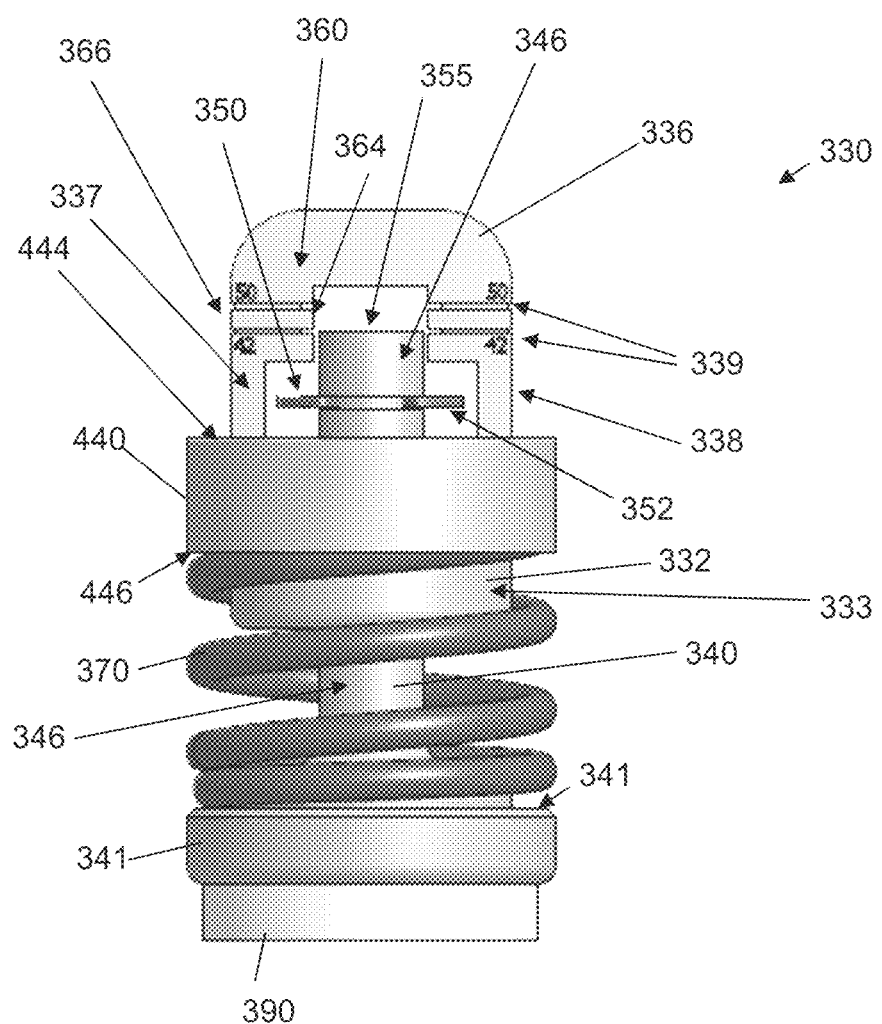
FIG. 14 is a front elevational view of one embodiment of a pressure monitor assembly employable with embodiments of the present invention.

As shown in the embodiments of FIGS. 12, 13 and 14, the upper frame arm 233 has a tip portion 440 formed at the end opposite the rear portion 442. The tip portion 440 can be formed in various shapes, and in various embodiments, can have a top face 444 having a width W that is wider than the width X of the top surface 434 of the upper frame arm 231. In this way, the tip portion 440 is suited to support the pressure monitor assembly 330. The tip portion 440 can be provided with an interior wall (not shown) forming an opening (not shown) in the tip portion 440 for receiving a trunk portion 335 of a clamp stem bushing 332 of the pressure monitor assembly 330. The upper frame arm tip 440 includes a top surface 444 and a bottom surface 446, and the pressure monitor assembly 330 includes a force indicator element 336 secured to and extending from the top surface 444 of the upper frame arm tip 440. As further shown in FIGS. 12 through 14, 18 and 19, the pressure monitor assembly further includes a clamp stem 340 having a base portion 341 and a stem portion 342, wherein the stem portion 342 is extendable through a central opening in the clamp stem bushing 332 and the upper frame arm tip portion 440, so as to be retained in movable relation therein. It will be appreciated that the clamp stem bushing 332 can be formed with a base portion 333 and a trunk portion 335, with the trunk portion 335 having an interior wall forming a substantially cylindrical channel therethrough for receiving the stem portion 342 of the clamp stem 340. The base portion 333 of the clamp stem bushing 332 can be appropriately sized to act as an alignment element for spring 370 when assembled and in operation. The stem portion 342 of the clamp stem 340 includes an outer wall 346, with a ridge 348 formed in the outer wall 346. The pressure monitor assembly 330 further includes a ring clip member 350 positioned within the ridge 348, wherein the ring clip member 350 includes a lower surface 352 engageable with the top surface 444 of the upper frame arm tip 440 and/or the trunk portion 335 of the clamp stem bushing 332. In this way, when the ring clip member 350 is engaged with the top surface 444 of the upper frame arm tip 440 and/or the trunk portion 335 of the clamp stem bushing 332, the device will have a pressure reading of zero. However, and as clamping action occurs on an element within the receiving area 275, the ring clip member 250 will rise from the top surface 444 and/or trunk portion 335, and the top edge 355 of the clamp stem portion 342 will rise to a measurable position proximate the force indicator element 336 secured to and extending from the top surface 444 of the upper frame arm tip 440.

As shown in the embodiments of FIGS. 12 through 14, the force indicator element 336 can be substantially U-shaped with a first arm 337 and a second arm 338 secured to the upper surface 444 of the upper frame arm tip 440, and further wherein the force indicator element 336 includes at least one insignia form 339 on at least one of the first 337 and second 338 arms. In various embodiments, each of the first 337 and second 338 arms includes a front face 360, a back face 362, an interior face 364 and an exterior face 366. Further, the insignia form 339 can be provided on one or more of the front face 360, back face 362, interior face 364 and exterior face 366 of one or both of the first 337 and second 338 arms. The insignia form 339 provides a mechanism for determining the amount of pressure being applied to an article in the receiving area of the device. For instance, the location of the clamp stem portion top edge 355 in relation to the insignia form(s) 339 can be viewed from all around the device, thereby permitting one or more individuals involved in the operation of the present invention to visually determine and measure the amount of pressure being applied to an article in the receiving area of the device. It will be appreciated that the insignia form can be one of many forms of marking, including a physical marking distinguished from the color or shade of the force indicator element 336, as well as a defacement and or indentation on the force indicator element 336.

As further shown in FIGS. 12 through 14, 18 and 19, the pressure monitor assembly can further comprise a pressure monitor spring member 370 positioned around the clamp stem 340 and between the top surface 372 of the clamp stem base portion 341 and the bottom surface 446 of the upper frame arm tip 440. The spring 370 assists in measuring the applied pressure to the article in the receiving area 275.

As further shown in FIGS. 14 and 19 through 21, the clamp stem base portion 341 of the clamp stem 340 can be provided with a top surface 372, top surface side wall 374, intermediate surface 376, intermediate side wall 378 and a bottom surface 380, wherein the bottom surface 380 has an opening 382 formed therein so as to form a compartment 384. In various embodiments, the bottom surface 380 has an internal radius Z, and the compartment 384 has an internal radius Y, wherein the compartment internal radius Y is larger than the bottom surface internal radius Z so as to permit the clamp stem 340 to retain various inserts, such as insert 390 in FIGS. 20 and 21.

Figure 21:
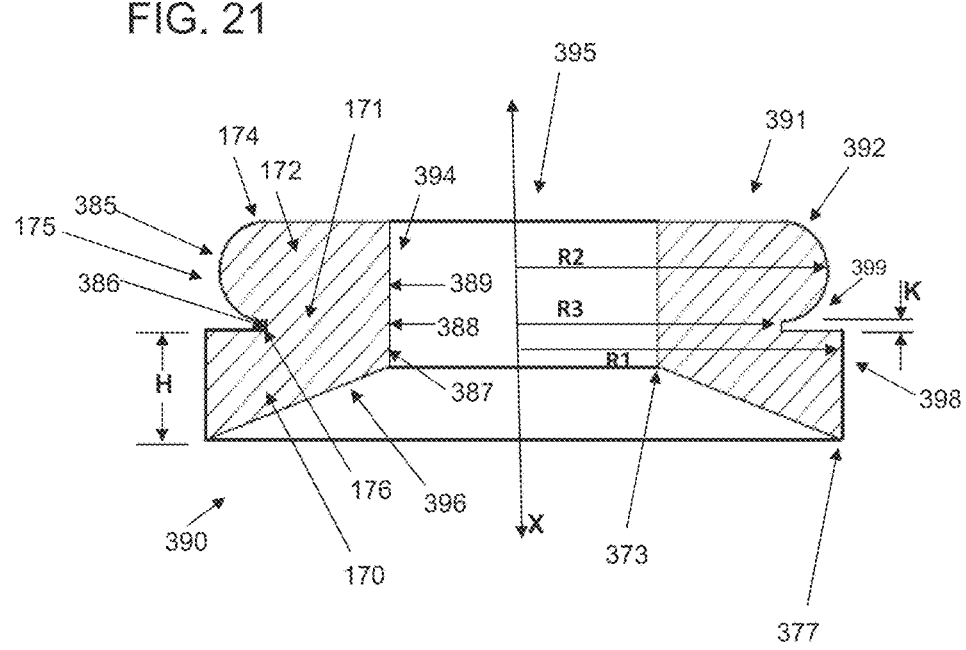
FIG. 21 is a cross-sectional view of the clamp stem insert element taken along the line 21-21 of FIG. 20.

As shown in FIG. 21, for example, the bushing insert can comprise a contact surface adapter 390 for the clamp device, and includes a body portion 170, a neck portion 171 and a head portion 172, wherein the body portion 170, neck portion 171 and head portion 172 each have an interior surface (387, 388 and 389, respectively) forming an opening 395 extending along an internal axis X of the bushing insert 390. In various embodiments, the body, neck and head portions are integrally formed as a monolithic unit. As shown in FIG. 21, the body portion 170 has an axially outer surface 396 and a radially outer surface 398, the neck portion 171 has a radially outer surface 386, and the head portion 172 has an axially outer surface 391 and a radially outer surface 385. The head portion and neck portion interior surfaces 389 and 388, along with a portion of the body portion interior surface 387, form a substantially cylindrical inner surface 394. The remainder of the body portion interior surface 387 can be a substantially frustoconical surface 396 to assist in providing a gripping and mating contact with the elements of the patella construct during operation, as described elsewhere herein.

Figure 20:
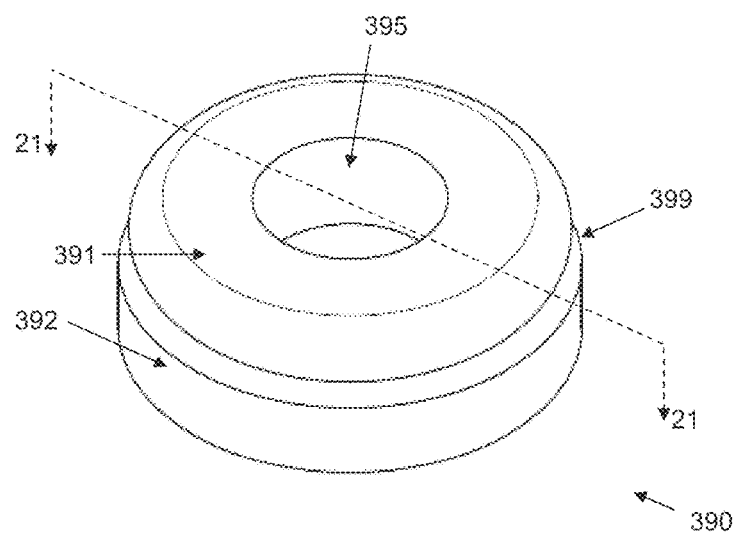
FIG. 20 is a perspective view of a clamp stem insert element according to embodiments of the present invention.

An exterior ledge 392 of the adapter 390 can be formed in the head portion 172 and can be substantially rounded as shown in FIGS. 20 and 21. Further, the radially outer surface 386 of the neck portion forms a catching notch 399 such that, when the adapter insert 390 is positioned into the compartment 384 of clamp stem 340, the catching notch 399 can engage the bottom surface lip 381 to snugly retain the insert 390 within the compartment 384. As shown in FIG. 21, the radial outer surface 386 of the neck portion can have an axial height H that is comparably smaller to the axial distances of the radial outer surfaces 385, 398 of the head and body portions, respectively, in order to facilitate snug and removable connection to the clamp stem as described herein. The varying shapes of the ledge 392, body portion external surface 398 and interior surfaces 394, 396 can assist with the deformability of the insert 390 to adapt to various uses as the insert 390 is deployed within the receiving area 275 of the device. In various embodiments, the body portion radially outer surface 398 has a height H that represents the length of the insert that is exposed beyond the side wall 378 of the clamp stem 340.

Figure 22:
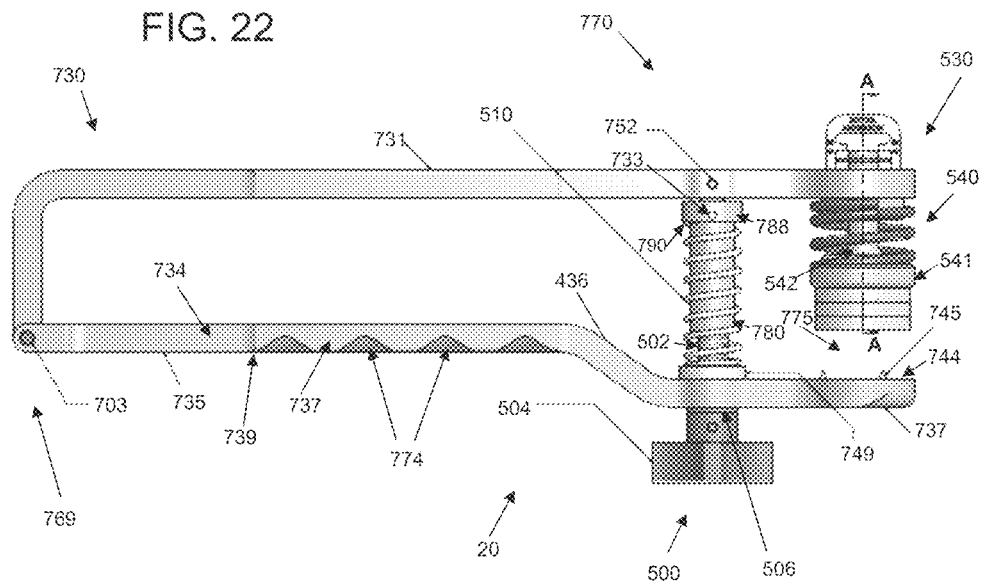
FIG. 22 is a front elevational view of an assembled version of another embodiment of the present invention.

As further shown in FIG. 21, the radially outer surface 385 of the head portion 172 has a radial distance R3 from the internal axis X, the radially outer surface 386 of the neck portion 171 has a radial distance R2 from the internal axis X, and the radially outer surface 398 of the body portion 170 has a radial distance R1 from the internal axis X. Further, the radial distance R1 of the body portion radially outer surface 398 is greater than the radial distance R3 of the head portion radially outer surface 385, and the radial distance R1 of the head portion radially outer surface 385 is greater than the radial distance R2 of the neck portion radially outer portion 386. In this way, the bushing insert 390 is positionable and snugly retained within the clamp stem 340 and 540 as shown in FIGS. 14 and 22.

In various embodiments, the radial distance R2 of the neck portion radially outer surface 386 and the radial distance R1 of the body portion radially outer surface 398 are substantially constant along the outer surfaces 386, 398 thereof, whereas the radial distance R3 of the head portion radially outer surface 385 is not constant along the outer surface thereof. As shown in FIG. 21, the head portion radially outer surface 385 has an axially outer end 174, an axially inner end 176 and an axial midsection 175, and the radial distance R3 of the head portion radially outer surface 385 is greater at the axial midsection 175 than at the axially outer 174 and inner 176 ends.

In various embodiments, the head portion radially outer surface 385 is substantially semi-circular in cross-section, as illustrated by ledge 392. The axially outer surface 396 of the body portion 170 has an axially inner edge 373 and an axially outer edge 377, and the axially outer surface 396 extends axially outwardly from the axially inner edge 373 to the axially outer edge 377. As further shown in FIG. 21, the axially outer surface 396 further extends radially outwardly from the axially inner edge 373 to the axially outer edge 377, and the body portion interior surface 387 extends from the neck portion interior surface 388 to the axially inner edge 373 of the axially outer surface 396 of the body portion 170.

Assembly of the embodiments of various components shown in FIGS. 12 through 21 can occur in several ways. Illustratively, the upper arm 231 and lower arm assembly 234 can be assembled and connected in hinged fashion as described above, wherein the upper arm can comprise a unitary body member, or alternatively can comprise a curved handle section 232 attached to a straight handle section 233. The lower arm assembly 234 can comprise a unitary body member, or alternatively an arrangement including a fixed end element 235, a bottom handle element 236 and one or more spacer elements 237. The fixed end element 235 can be joined with the one or more spacer elements, which are then joined with the bottom handle element. The pivot nut 280 can then be pivotally connected to the fixed end element 235 using pin 297, with the spring 310 inserted over the outer surface 284 of the pivot nut 280. Knob assembly 300 can comprise knob 304 passing through washer 306, with the threaded screw portion 302 of the knob assembly passing through the upper arm assembly 231 and into the pivot nut body portion, where the screw portion 302 can threadingly engage the pivot nut 280. In this way, the upper frame arm and lower frame arm assembly can be locked in a specific location and force can be applied therebetween.

The pressure monitor assembly 330 can then be affixed to the clamp assembly in various fashions. For instance, an insert 390 can be pushed into the compartment 384 of the clamp stem 340. The clamp stem bushing 332 can be fitted and secured through the opening in the upper arm tip portion 440, such as through welding, glue or other methods, the spring 370 can be placed around the stem portion 341 of the clamp stem 340, as well as around the base portion 333 of the clamp stem bushing 332, and the clamp stem 340 can then be fitted through the stem bushing. Once the clamp stem 340 is through the upper arm tip portion 440, the ring member 350 can be secured within the ridge 348 of the clamp stem 340, thereby keeping the clamp stem secured to the upper arm tip portion as the lower surface 352 of the ring member 350 contacts the top surface 444 of the upper arm tip portion 440. The force indicator 336 can then be affixed to the upper arm tip portion 440. It will be appreciated that the above described illustrations of assembly can be performed in a variety of ways, and the particular order of operation described above is not the sole order for assembly.

In operation of the embodiments shown in FIGS. 12 through 21, an article to be clamped, such as a patella construct, can be placed in the receiving area 275 of the clamp device. In various embodiments, the article is first measured so as to determine an appropriately sized insert 390 to employ. For instance, a thin article may require a larger insert 390, whereas a thicker article may require a smaller insert 390. In various embodiments, multiple inserts 390 of different heights H are employed and can be interchanged within clamp stem 340. For example, a first size insert can be provided with a height H ranging from approximately 25.5 mm to approximately 30 mm, a second size insert can be provided with a height H ranging from approximately 21 mm to approximately 25 mm, and a third size insert can be provided with a height H ranging from approximately 15 mm to approximately 20.5 mm. it will be appreciated that the inserts may be provided with different heights H, with broader dimensional ranges of height H, with tighter dimensional ranges of height H, as a set of two inserts, three inserts, or any number of inserts deemed appropriate for a given application.

A portion of the article may be placed on the spike elements of the fixed end element 235 of the lower arm assembly 234. A medical professional, after any necessary intermediate steps, such as securing bone cement or performing some other process on the article, can then rotate the knob 304 so as to bring the pressure monitor assembly 330 onto the article and/or to apply additional pressure on the article. In this way, the upper frame arm and lower frame arm assembly can be locked in a specific location and force can be applied therebetween. The dual spring action of spring 310 about the pivot nut 280 and spring 370 about the clamp stem 340 acts to resist the tension being applied by the user. Once sufficient pressure is applied to the article, any additional force applied through the knob assembly 300 will result in the clamp stem 340 extending upwardly through the upper arm tip portion 440, whereby the top edge 355 of the clamp stem portion 342 will rise to a measurable position proximate the force indicator element 336 secured to and extending from the top surface 444 of the upper frame arm tip 440. It will be appreciated that the location of the clamp stem portion top edge 355 in relation to the insignia form(s) 339 can be viewed from all around the device, thereby permitting one or more individuals involved in the operation of the present invention to visually determine and measure the amount of pressure being applied to an article in the receiving area of the device. Once the top edge 355 is at a desired measured pressure, as indicated by its location adjacent the insignia form(s) 339, the professionals can monitor the pressure to ensure that any pressure adaptations necessary for the required environment can be exacted through the knob assembly. For instance, if a particular procedure requires that forty-two pounds of pressure be applied for seven minutes, and if the pressure reaches a measurement of forty-two pounds for one minute, then begins to drop, the user can rotate the knob 304 to add pressure, and watch the clamp stem portion top edge 355 to ensure it reaches the forty-two pound line on the indicator 336. Similar monitoring and adjustments can occur through the seven minute duration, or whatever duration is required for a particular procedure. When the procedure is complete, the device can be loosened through the knob assembly, and the knob can even be substantially or even entirely disengaged from the pivot nut if necessary to allow an article to be properly removed from the receiving area.

It will be appreciated that the present invention can provide different forms of gauging pressure, including a light-emitting diode (LED) or other visual indicator, an auditory indicator, or other form of indicator in lieu of or in addition to the pressure indicating element 336 shown and described herein. It will also be appreciated that various embodiments of devices described herein can employ air, water, nitrogen and other fluids in applying hydraulic pressure. Further, the device embodiments are adaptable to incorporate electrically and/or battery-powered elements to apply and remove pressure. In still other embodiments, plasma pressure, CNC technologies and/or photoelastics can be employed. Additionally, the assembly embodiments described herein incorporating the upper and lower arm assemblies can be adapted to implement and measure a pulling force, to the extent a pulling force is desired on a given article instead of a clamping force.

Figure 24:
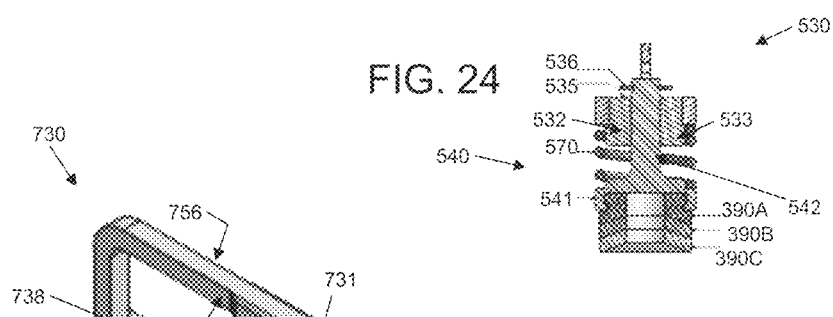
FIG. 24 is a cross-sectional view of a pressure monitor assembly according to embodiments of the present invention, as taken along the line A-A of FIG. 22.
Figure 23:
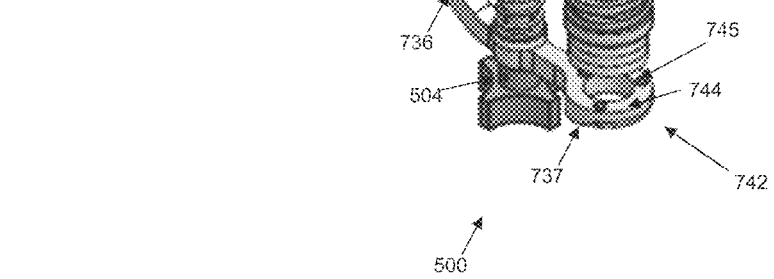
FIG. 23 is a perspective view of the embodiment of FIG. 22.

FIGS. 22 through 24 show an additional embodiment of the adjustable measured applied pressure clamp device 20 employable with embodiments of the present invention. As shown in the embodiment in FIG. 22, the device 20 comprises a frame assembly 730 for receiving and maintaining a clamp assembly 770, which can include a knob assembly 500 and a pressure monitor assembly 530. Whereas the embodiment of the invention in FIGS. 12 through 17 shows knob assembly 300 secured through the upper arm 231 and pivot nut 280 movably secured to the lower arm 234, the embodiment of the invention shown in FIGS. 22 through 23 shows knob assembly 500 secured through the lower arm 734 and pivot nut 780 movably secured to the upper arm 731.

As shown in the embodiment of FIGS. 22 and 23, the frame assembly 730 can include an upper frame arm 731 and a lower frame arm 734. In various embodiments, the upper frame arm 731 and lower frame arm 734 comprise independent monolithic units. In other embodiments of the present invention, the upper frame arm 731 and lower frame arm 734 can comprise multiple elements. The upper frame arm 731 can be referred to herein as an upper frame arm assembly and the lower frame arm 734 can be referred to herein as a lower frame arm assembly, regardless of whether each comprises a single monolithic unit or a multi-element arrangement. As shown, for example, in FIGS. 22 and 23, the lower frame arm assembly 734 comprises a unitary arm having a handle portion 735, an angled intermediate portion 736 and an end portion 737. The end portion 737 can have substantially the same configuration as fixed end element 235 of FIG. 17, as described elsewhere herein. For example, the end portion 737 can be provided with a top surface 444 adapted to receive one or more spike elements 745 for receiving and securing elements of a patella construct or other item to be clamped or otherwise manipulated in the receiving area 775, in accordance with the present invention. For instance, the top surface 744 of the clamp support portion 742 can be provided with openings similar to openings 248 as shown in FIG. 17 and described elsewhere herein.

In the embodiment shown in FIGS. 22 through 23, contrary to the embodiment shown in FIGS. 12, 13 and 17, the end portion 737 of arm 733 is not provided with a slot adapted to receive a pivot nut. Rather, such a slot 750 is provided in upper frame arm 731, as shown in FIG. 23. A side opening 752 is also shown extending from a first side wall 754 to a second side wall 456 of the upper arm 731, and the side opening 752 also passes through slot 750. Slot 750 is adapted to receive a pivot nut 780 and pin 733, so as to allow the pivot nut 780 to be movably secured to the upper arm 731, similar to how pivot nut 280 is movably secured to the extension portion 240 of the fixed end element 235 of lower arm 231 in connection with the embodiment shown in FIGS. 12 through 17.

As shown in FIGS. 22 and 23, the rear portion 769 of the lower frame arm assembly 734 is hingedly connected to the upper frame arm 731, such as by a pin 703 extending through openings in the upper 734 and lower 731 frame arms. The handle section 735 of the lower frame arm 731 (and optionally portions of the upper frame arm 734) can further be provided with indentations or other forms of gripping elements 774 to facilitate operation. The handle section 735 includes side wall surfaces 737, a top surface 738 and a bottom surface 739, and in various embodiments, the indentations 774 are on one or more of the side wall surfaces 737. It will be appreciated that the hinged connection of upper 734 and lower 731 arms, along with the sloped arrangement of lower arm 731 facilitates the meeting of substantially parallel opposing forces in the receiving area 775, during operation of the clamp assembly 770 of the present invention.

As shown in the embodiments of FIGS. 22 through 24, the clamp assembly 770 includes a pivot nut 780, a knob assembly 500 and a spring member 510, with the pivot nut 780 pivotally secured to the upper frame arm assembly 731, as described above. In various embodiments, the spring member 510 and the pivot nut 780 can be considered part of the knob assembly 500 of embodiments of the present invention. The pivot nut 780 can be substantially the same as pivot nut 280 shown in FIGS. 15 and 16 and described above, including at least an axially outer portion 291 of the interior wall 286 that is threaded so as to be capable of threadedly receiving an adjustment screw portion 502 of the knob assembly 500. The threaded engagement of the adjustment screw portion 502 of the knob assembly 500 with the interior 286 of the pivot nut body portion 282 permits the embodiments to operate so as to provide increasing or decreasing clamping pressure to the article in the receiving area 775, for example. The adjustment screw 502 can be provided similar to the adjustment screw 302 of the knob assembly 300 shown and described in connection with FIGS. 12 and 13, for example. A knob 504 and a washer element 506 can also be provided similar to knob 304 and a washer element 306 shown in FIGS. 12 and 13. Rotation of the knob 504 in one direction (e.g., clockwise) results in a tighter engagement of the screw 502 with the pivot nut 780, and rotation of the knob 504 in the opposite direction (e.g., counterclockwise) results in a loosening of the engagement between the screw 502 and pivot nut 780. Loosening thereby permits the upper arm 731 to raise higher, thereby permitting more space in the receiving area 775. As further shown in FIGS. 22 and 23, the spring member 510 can be positioned about the exterior wall of the pivot nut body 780, engaging the head surface 790 of the pivot nut head portion 288, and also engaging the top surface 744 of lower arm 734, or alternatively a washer 749 positioned between top surface 744 and spring 510.

As shown in the embodiments of FIGS. 22 through 24, the pressure monitor assembly 530 can be provided similarly to assembly 330 of FIGS. 12 through 14, including a clamp stem 540 with a base portion 541 and stem portion 542, a clamp stem bushing 532 having a trunk portion 535, and further including a force indicator element 536. The upper frame arm 731 can be formed similar to upper frame arm 233 as described above and shown in FIGS. 12 and 13, for example, in order to fittingly receive the pressure monitor assembly 530 for operation as described herein, wherein the clamp stem portion 542 is extendable through a central opening in the clamp stem bushing 532 and the upper frame arm tip portion 440 of the upper arm 233, so as to be retained in movable relation therein. It will be appreciated that the clamp stem bushing 532 can be formed with a base portion 533 and a trunk portion 535, with the trunk portion 535 having an interior wall forming a substantially cylindrical channel therethrough for receiving the stem portion 542 of the clamp stem 540. The base portion 533 of the clamp stem bushing 532 can be appropriately sized to act as an alignment element for spring 570 when assembled and in operation. The stem portion 542 of the clamp stem 340 can have a ridge formed in the outer wall, and the pressure monitor assembly 530 can further includes a ring clip member positioned within the ridge, wherein the ring clip member includes a lower surface engageable with the top surface of the upper frame arm tip and/or the trunk portion 535 of the clamp stem bushing 532. In this way, when the ring clip member is engaged with the top surface of the upper frame arm tip and/or the trunk portion 535 of the clamp stem bushing 532, the device will have a pressure reading of zero. However, and as clamping action occurs on an element within the receiving area 775, the ring clip member will rise from the top surface and/or trunk portion 535, and the top edge of the clamp stem portion 542 will rise to a measurable position proximate the force indicator element 536 secured to and extending from the top surface of the upper frame arm tip. It will be appreciated that the clamp stem bushing can also be integrated into the upper arm assembly 431/731 instead of being a separate part.

The pressure monitor spring member 570 can be positioned around the clamp stem 540 and between the top surface of the clamp stem base portion 541 and the bottom surface of the upper frame arm tip. The spring 570 assists in measuring the applied pressure to the article in the receiving area 775.

Figure 18:
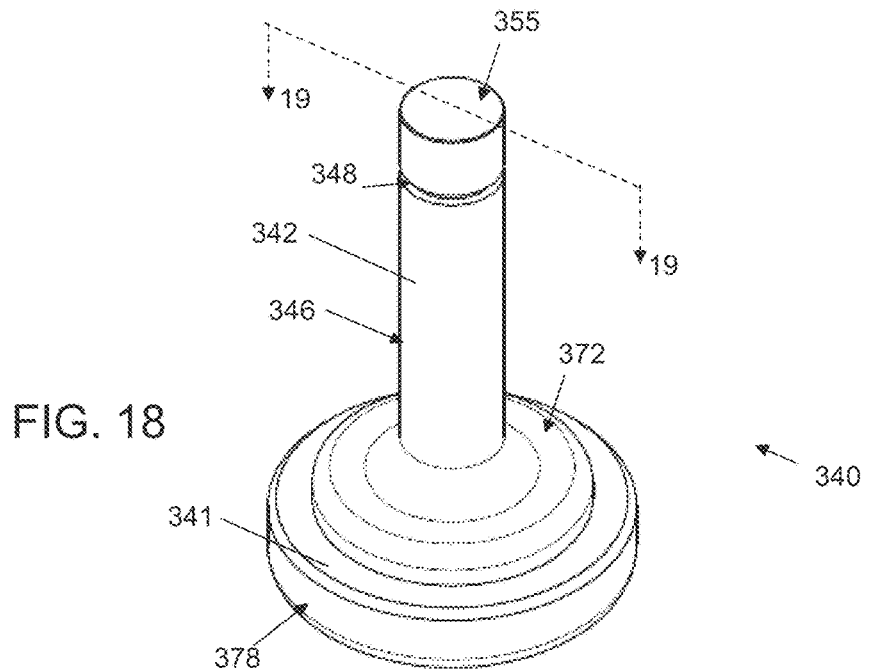
FIG. 18 is a perspective view of one embodiment of a clamp stem element employable with embodiments of the present invention.
Figure 19:
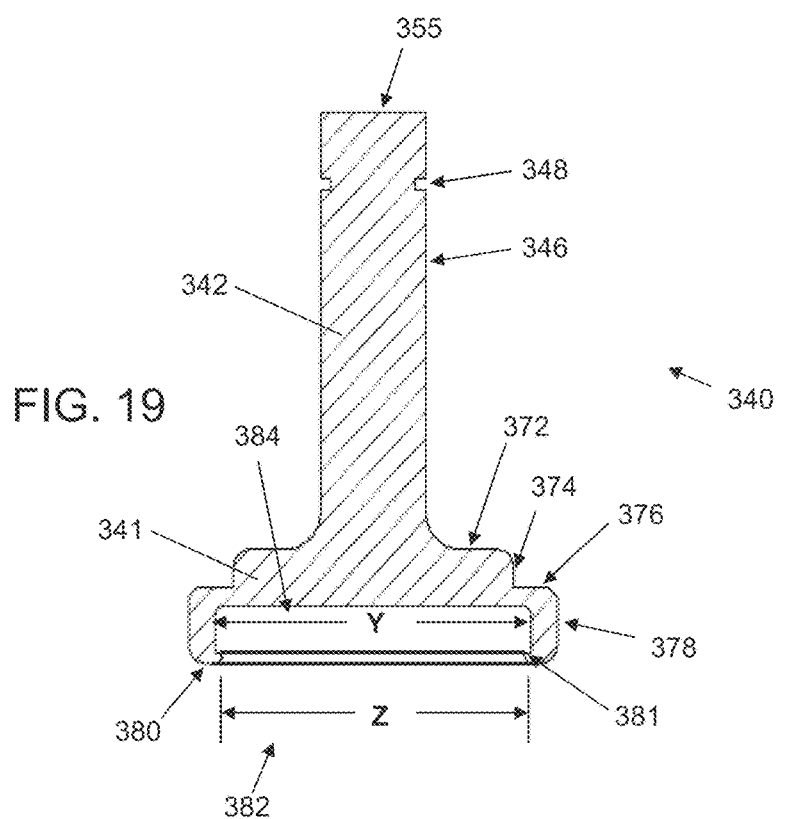
FIG. 19 is a cross-sectional view of the clamp stem element taken along the line 19-19 of FIG. 18.

The description of the clamp stem and its surfaces in connection with FIGS. 18 and 19 above are applicable to the clamp stem 540 shown and described in connection with FIGS. 22 through 24. Thus, as described above, the clamp stem base portion 341 of the clamp stem 340 can be provided with a top surface 372, top surface side wall 374, intermediate surface 376, intermediate side wall 378 and a bottom surface 380, wherein the bottom surface 380 has an opening 382 formed therein so as to form a compartment 384. In various embodiments, the bottom surface 380 has an internal radius Z, and the compartment 384 has an internal radius Y, wherein the compartment internal radius Y is larger than the bottom surface internal radius Z so as to permit the clamp stem 340 to retain various bushing inserts, such as insert 390 in FIGS. 20 and 21. FIGS. 22 through 24 illustrate multiple bushing inserts 390A, 390B and 390C inserted into the clamp stem 540. While elements 390A, 390B and 390C can be formed so as to engage one another in a nested arrangement, it will be appreciated that different bushing inserts of different dimensions can be provided so as to adapt for smaller, medium-sized and larger patella constructs during operation of the device. Accordingly, in various embodiments, bushing insert 390 of FIG. 21 can be used for patella thicknesses that range from approximately 25.5 mm to 30 mm in a larger embodiment, patella thicknesses that range from approximately 21 mm to 25 mm in a medium embodiment, and patella thicknesses that range from approximately 15 mm to 20.5 mm in a smaller embodiment, so as to provide clamping ability with accurate alignment as described herein.

In various embodiments, each bushing insert 390 can be made of rubber and can be provided for a single use. In this way, proper cleaning and sterilization of the metal device 20 is facilitated for each surgery, with the chances of cross-contamination between surgeries being minimized. In various embodiments, the same three thickness bushing inserts can also be molded on the implant side to match the exact shape of different manufactures of anatomical patella implants. When an anatomical implant is used a tab or specific feature is molded onto or in the bushing insert allowing exact radial alignment between the anatomical rubber insert and anatomical implant.

As shown in FIGS. 25 through 28, the present invention can operate whereby, instead of an insert 390 as shown in FIG. 21, a bushing adapter device 880 is provided that fits around the clamp stem base portion 811 instead of fitting into an opening in the clamp stem base portion. In such embodiments, the bushing 880 includes a head portion 893 mounted around the side wall 810 of the clamp stem base portion 811, and the clamp stem base portion 811 does not have an opening therein.

Figure 25:
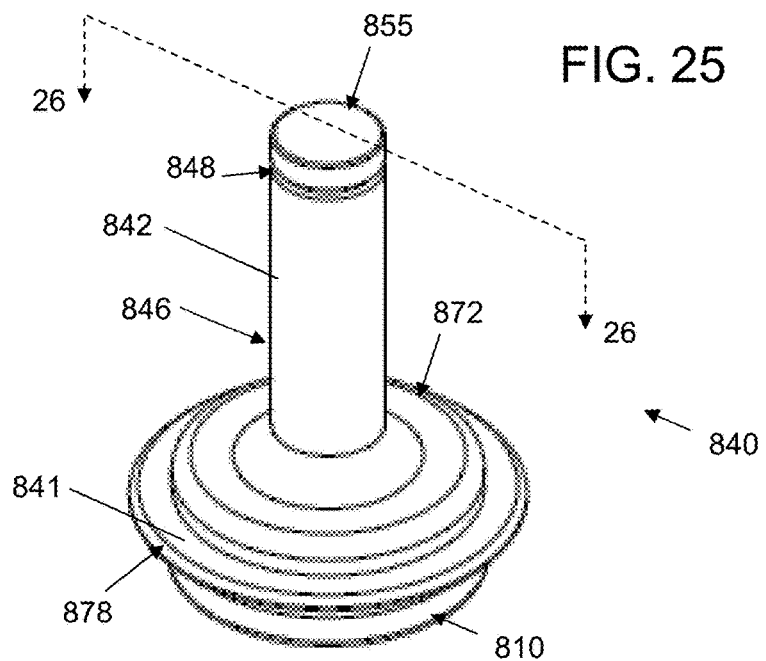
FIG. 25 is a perspective view of an alternative embodiment of a clamp stem element employable with embodiments of the present invention.
Figure 26:
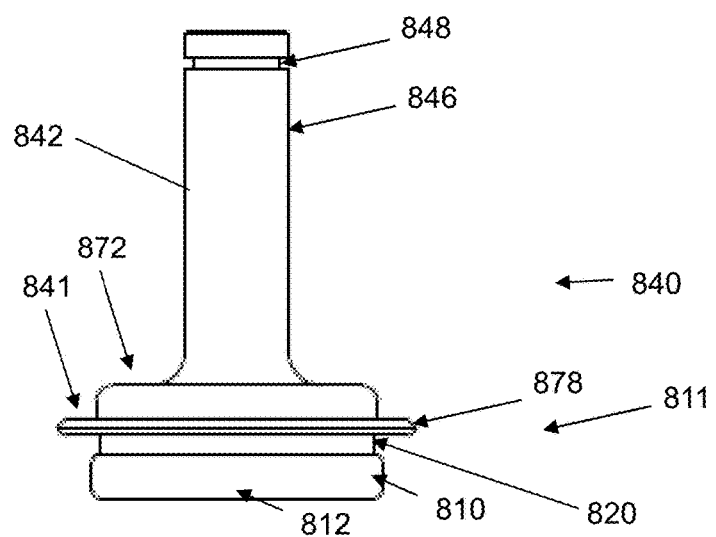
FIG. 26 is a cross-sectional view of the clamp stem element taken along the line 26-26 of FIG. 25.

As shown in FIGS. 25 and 26, the additional embodiment of the clamp stem 840 includes a base portion 811 and a stem portion 842 having an outer surface 846, a ridge 848 and a top surface 855. The base portion 811 has a top surface 872, a bottom side wall 810 and an intermediate ring 878 having a top surface 841. An intermediate side wall 820 is positioned between the intermediate ring 878 and the bottom side wall 810.

Figure 27:
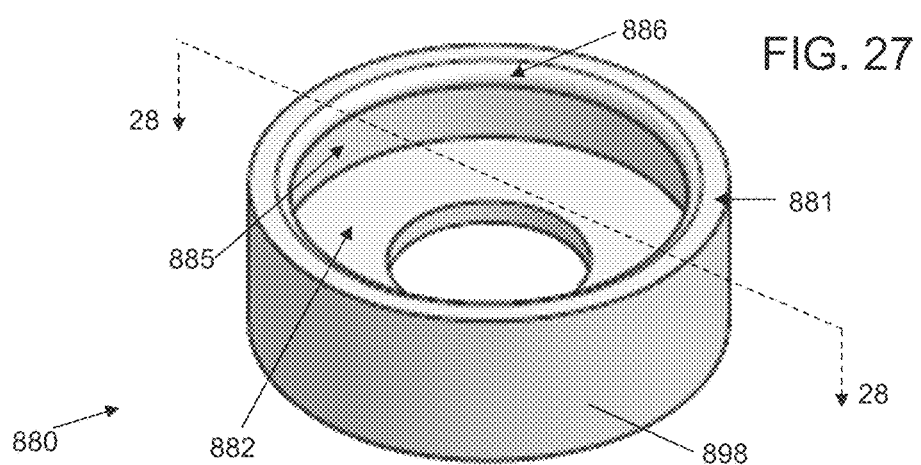
FIG. 27 is a perspective view of a clamp stem insert element in accordance with embodiments of the present invention.
Figure 28:
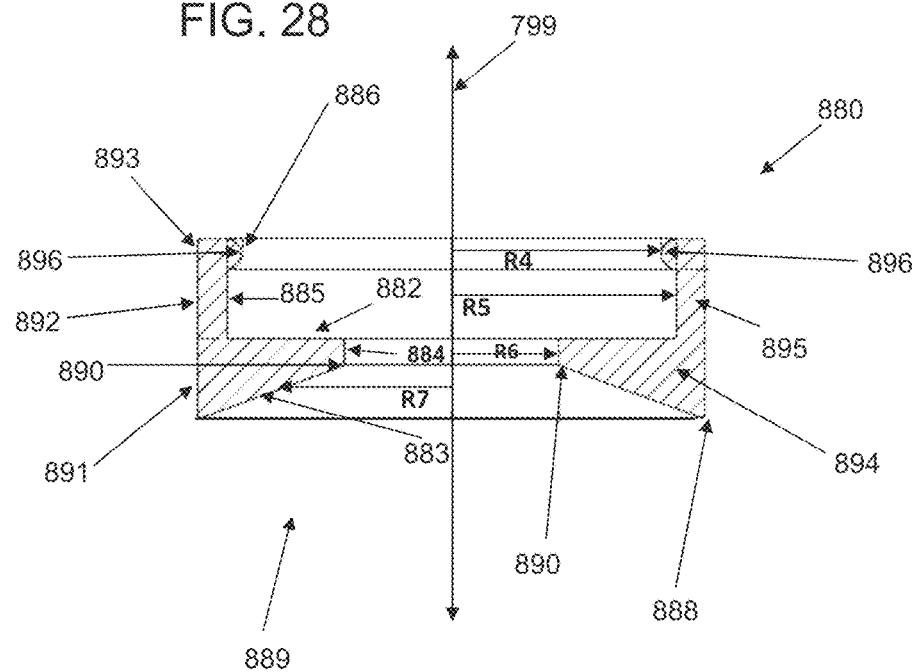
FIG. 28 is a cross-sectional view of the clamp stem insert element taken along the line 28-28 of FIG. 27.
Figure 29:
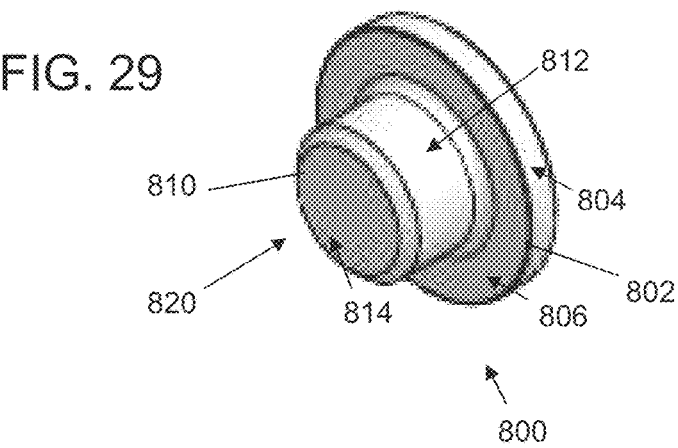
FIG. 29 is a perspective view of a clamp base insert element according to an embodiment of the present invention.
Figure 30:
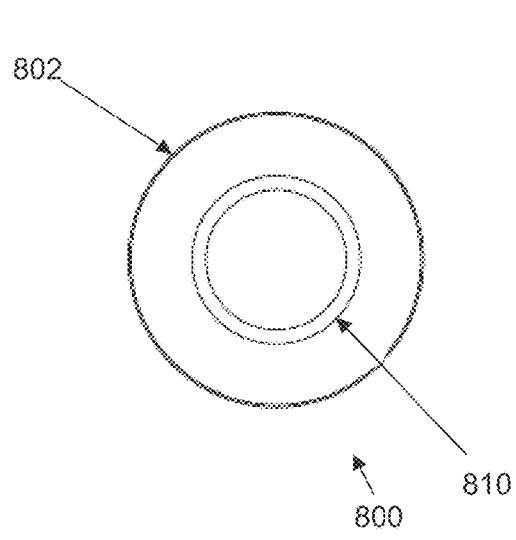
FIG. 30 is a front view of the clamp base insert element of FIG. 29.

As shown in FIGS. 27 and 28, the additional embodiment of the bushing adapter 880 includes a top wall 881, an outer wall 898, a clamp stem engaging surface 882, a body portion 894, a neck portion 895 and a head portion 896. In various embodiments, the body, neck and head portions are integrally formed as a monolithic unit. The body portion 894 has a radially inner surface 884 and a radially outer surface 891, the neck portion 895 has a radially inner surface 885 and a radially outer surface 892 and the head portion 896 has a radially inner surface 886 and a radially outer surface 893. The body portion 894 further has an axially outer surface 883 that extends from an axially inner edge 890 to an axially outer edge 888 so as to form a substantially frustoconical opening 889. The frustoconical opening assists in providing a gripping and mating contact with the elements of the patella construct during operation, as described elsewhere herein. The radially inner surface 886 of the head portion 896 forms an interior ledge that assists in secure retention around the side wall 810 of the clamp stem as described elsewhere herein.

As further shown in FIG. 28, the radially inner surface 886 of the head portion 896 has a radial distance R4 from the internal axis 799, the radially inner surface 885 of the neck portion 895 has a radial distance R5 from the internal axis 799, the axially inner portion of the radially inner surface 884 of the body portion 894 has a radial distance R6 from the internal axis 799, and the axially outer portion of the radially inner surface 884 of the body portion has a radial distance R7 from the internal axis. As further shown in FIG. 28, the radial distance R4 and the radial distance R7 are variable, and the radial distances R5 and R6 are substantially constant. Further, the radial distance R4 is less than the radial distance R5, and the radial distance R6 is less than the radial distances R4 and R5. In this way, the bushing adapter 888 is not only positionable and snugly retained around the clamp stem 840 but also provides a contact surface at the axially outer surface 883 of the body portion 884 that assists in providing a gripping and mating contact with the elements of the patella construct or other elements during operation.

In various embodiments, the radially inner surface and/or interior ledge 886 of the head portion 896 can be substantially semi-circular and/or rounded in cross-section as shown in FIGS. 27 and 28, and forms a catching notch that snugly engages the intermediate wall of the clamp stem as described elsewhere herein. The varying shapes of the head portion 896, neck portion 895 and body portion 894 assist with the deformability of the bushing adapter 888 to adapt to various uses as the adapter (with clamp stem, for example) is deployed above the receiving area 275 of the device.

In various embodiments, the axially outer surface 883 of the body portion 894 extends axially outwardly from the axially inner edge 890 to the axially outer edge 888. As further shown in FIG. 28, the axially outer surface 883 further extends radially outwardly from the axially inner edge 890 to the axially outer edge 888, and the body portion interior surface 884 extends from the clamp stem engaging surface 882 to the axially inner edge 890 of the axially outer surface 883 of the body portion 894. In various embodiments, the radial distances to each of the radially outer surfaces 892 and 893 of at least the neck portion 895 and head portion 896 are substantially the same. In various additional embodiments, the radial distances to each of the radially outer surfaces 891, 892 and 893 of the body portion 894, neck portion 895 and head portion 896 are substantially the same, thereby providing a substantially cylindrical outer surface to the adapter 880.

In operation, the adapter 888 of FIGS. 27 and 28 can be positioned around the bottom side wall 810 of the clamp stem 840 of FIGS. 25 and 26, such that the radially inner surface 886 of the head portion 896 of the adapter 888 engages the intermediate side wall 820 of the clamp stem 840 and the radially inner surface 885 of the neck portion 895 of the adapter 888 engages the bottom side wall 810 of the clamp stem 840. The clamp stem engaging surface 882 engages the bottom surface 812 of the clamp stem 840. In this way, the adapter 888 is securely retained about the clamp stem base 811 and can appropriately engage elements of the patella construct or other elements brought into the clamping area to be clamped.

It will further be appreciated that the present invention can be adapted such that the spike elements 745 are positioned on the clamp stem base portion 341/541/811 depending from the upper arm 231 and the insert(s) 390 are provided on the lower arm 234.

Figure 31:
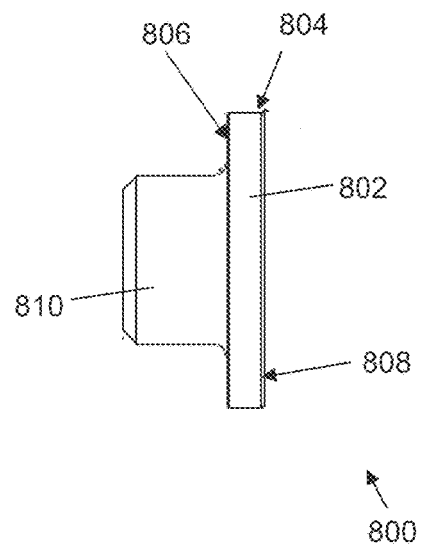
FIG. 31 is a right side view of the clamp base insert element of FIG. 29.

As shown in FIGS. 31 through 33, in another embodiment of the present invention, an installation cap 800 is provided for assistance with proper setup and operation of the present invention. The cap 800 can be provided with a base 802 having a side wall 804, a top wall 806 and a back wall 808, and is further provided with a substantially cylindrical trunk 810 having an outer surface 812 and an inner surface 814 that defines an opening 820 extending through the cap 800. Edges of the base 802 and trunk 810 portions can be chamfered to provide a finished element with a surface that may be more readily engaged by a finger, fingernail or other element capable of poking the cap from its initially installed position. The cap 800 can be installed in the opening 830 of the fixed end element 235 of the lower frame arm assembly 234/734 such that the trunk outer surface 812 engages the inner surface of the fixed end element 235 defining the opening 830. In this way, the base 802 of the cap 800 extends into the receiving area 775 between the fixed end element 235 (FIGS. 12-13) or end element 737 of lower frame arm 734 (FIGS. 22-23) and the insert 390. The base 802 also covers up the spike elements 745, such that a user that seeks to install an insert 390 just before a procedure is to take place will be protected from minor abrasion.

It will further be appreciated that various embodiments of the present invention can employ various material types, including but not restricted to stainless steel, aluminum, brass, plastics and high strength composites, for example.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

The invention claimed is:

1. A contact surface adapter for a clamp, comprising:
a bushing having a body portion, a neck portion and a head portion, wherein the body portion, neck portion and head portion each have an interior surface forming an opening extending along an internal axis of the bushing, wherein the body portion has an axially outer surface and a radially outer surface, the neck portion has a radially outer surface, and the head portion has an axially outer surface and a radially outer surface;
wherein the axially outer surface of the body portion has an axially inner edge and an axially outer edge, and wherein the axially outer surface extends axially outwardly from the axially inner edge to the axially outer edge; and
an installation cap having a base and a substantially cylindrical trunk, wherein the trunk has an outer surface, and further includes an inner surface that defines an opening extending through the cap.

2. The adapter of claim 1, wherein the axially outer surface further extends radially outwardly from the axially inner edge to the axially outer edge.

3. The adapter of claim 1, wherein the head portion, neck portion and body portion are integrally formed as a monolithic unit, wherein the radially outer surface of the head portion has a radial distance from the internal axis, the radially outer surface of the neck portion has a radial distance from the internal axis, and the radially outer surface of the body portion has a radial distance from the internal axis, and further wherein the radial distances of each of the outer surfaces of the head portion, neck portion and body portion are substantially the same.

4. The adapter of claim 1, wherein the radially outer surface of the head portion has a radial distance from the internal axis, the radially outer surface of the neck portion has a radial distance from the internal axis, and the radially outer surface of the body portion has a radial distance from the internal axis, and further wherein the radial distance of the body portion radially outer surface is greater than the radial distance of the head portion radially outer surface, and wherein the radial distance of the head portion radially outer surface is greater than the radial distance of the neck portion radially outer surface.

5. The adapter of claim 1, further including a clamp stem having a base portion and a stem portion, wherein the clamp stem base portion includes a top surface and a bottom surface, wherein the bushing is removably secured to the base portion of the clamp stem.

6. The adapter of claim 1, wherein the clamp stem base portion includes \ an outer wall, and wherein the bushing adapter head portion is removably secured around the clamp stem base portion outer wall.

7. The adapter of claim 1, wherein the axially outer surface of the body portion has an axially inner edge and an axially outer edge, and wherein the axially outer surface extends axially outwardly from the axially inner edge to the axially outer edge.

8. The adapter of claim 7, wherein the axially outer surface further extends radially outwardly from the axially inner edge to the axially outer edge.

9. A contact surface adapter for a clamp, comprising:
a bushing having a body portion, a neck portion and a head portion, wherein the body portion, neck portion and head portion each have an interior surface forming an opening extending along an internal axis of the bushing, wherein the body portion has an axially outer surface and a radially outer surface, the neck portion has a radially outer surface, and the head portion has an axially outer surface and a radially outer surface;
wherein the radially outer surface of the head portion has a radial distance from the internal axis, the radially outer surface of the neck portion has a radial distance from the internal axis, and the radially outer surface of the body portion has a radial distance from the internal axis, and further wherein the radial distance of the body portion radially outer surface is greater than the radial distance of the head portion radially outer surface, and wherein the radial distance of the head portion radially outer surface is greater than the radial distance of the neck portion radially outer surface; and
an installation cap having a base and a substantially cylindrical trunk, wherein the trunk has an outer surface, and further includes an inner surface that defines an opening extending through the cap.

10. A contact surface adapter for a clamp, comprising:
a bushing having a body portion, a neck portion and a head portion, wherein the body portion, neck portion and head portion each have an interior surface forming an opening extending along an internal axis of the bushing, wherein the body portion has an axially outer surface and a radially outer surface, the neck portion has a radially outer surface, and the head portion has an axially outer surface and a radially outer surface, wherein the head portion, neck portion and body portion are integrally formed as a monolithic unit, wherein the radially outer surface of the head portion has a radial distance from the internal axis, the radially outer surface of the neck portion has a radial distance from the internal axis, and the radially outer surface of the body portion has a radial distance from the internal axis, and further wherein the radial distances of each of the outer surfaces of the head portion, neck portion and body portion are substantially the same;
wherein the axially outer surface of the body portion has an axially inner edge and an axially outer edge, and wherein the axially outer surface extends axially outwardly from the axially inner edge to the axially outer edge; and
an installation cap having a base and a substantially cylindrical trunk.

* * * * *